United States Patent [19]
Houghten et al.

[11] Patent Number: 5,783,577
[45] Date of Patent: Jul. 21, 1998

[54] SYNTHESIS OF QUINAZOLINONE LIBRARIES AND DERIVATIVES THEREOF

[75] Inventors: Richard A. Houghten, Del Mar; John M. Ostresh, Encinitas, both of Calif.

[73] Assignee: Trega Biosciences, Inc., San Diego, Calif.

[21] Appl. No.: 713,409

[22] Filed: Sep. 13, 1996

Related U.S. Application Data

[60] Provisional application No. 60/031,290 Sep. 15, 1995.
[51] Int. Cl.$^6$ ............... A61K 31/495; C07D 237/00; G01N 33/00
[52] U.S. Cl. ............... 514/247; 514/259; 436/518; 436/97; 436/96; 436/98; 436/111; 544/224; 544/235
[58] Field of Search ............... 436/518, 91, 96, 436/98, 111; 514/259; 544/224, 235

[56] References Cited

U.S. PATENT DOCUMENTS

| | | | |
|---|---|---|---|
| 5,010,175 | 4/1991 | Rutter et al. | 530/334 |
| 5,182,366 | 1/1993 | Huebner et al. | 530/334 |
| 5,430,148 | 7/1995 | Webber et al. | 544/238 |

OTHER PUBLICATIONS

Gordon et al., "Applications of combinatorial technologies to drug discovery. 2. Combinatorial organic synthesis, library screening strategies, and future directions." *J. of Med. Chem.*, 37(10):1386–1401 (1994).

Gallop et al., "Applications of combinatorial technologies to drug discovery. 1. Background and peptide combinatorial libraries." *J. of Med. Chem.*, 37(9):1233–1251 (1994).

Houghten et al., "Generation and use of synthetic peptide combinatorial libraries for basic research and drug discovery." *Nature*, 354:94–96 (1991).

Goff and Zuckermann, "Solid–phase synthesis of highly substituted peptide 1(2H)–Isoquinolinones." *J. Org. Chem.*, 60:5748–5749 (Sep. 8, 1995).

Misra et al., "Anticonvulsant and monoamine oxidase inhibitory properties of newer chlorostrylquinazolones." *Pharm. Res. Comm.*, 11(7):623–633 (1979).

Kort and Lamchen, "Preparation and properties of some substituted quinazolino [3.2–b]–cinnolines." *J. Chem. Soc.*, (C):2190–2196 (1966).

Ostresh et al., "Libraries from libraries: Chemical transformation of combinatorial libraries to extend the range and repertoire of chemical diversity." *Proc. Natl. Acad. Sci. USA*, 9:11138–11142 (1994).

Dooley et al., "Identification of tetrameric opioid peptides from a combinatorial library composed of L–,D–and non–proteinogenic amino acids." *Peptides 1994*: Proceedings of the Twenty–Third European Peptide Symposium Sep. 4–10, 1994, Braga, Portugal.

Meyer and Wagner, "The Niementowski reaction, the use of methyl anthranilate or isatoic anhydride with substituted amides or amidines in the formation of 3–substituted–4–keto–3, 4–dihydroquinazolines. The course of the reaction." *J. Of Organic Chem.*, 239–252 (1943).

Grimmel et al., "Phosphazo compounds and their use in preparing amides." *J. of the American Chem. Soc.*, 68(4):539–543 (1946).

Parmar and Seth, "Selective inhibition of nicotinamide adenine dinucleotide dependent oxidation by 2–methyl–3–o–Tolyl–4–Quinazolone." *Canadian J. of Biochem.*, 43:1179–1185 (1965).

Joshi et al., "Fluorinated quinazolones:synthesis & CNS activity of fluorinated quinazolone derivatives." *Indian J. Exp. Biol.*, 15:1064–1066 (1977).

Leszkovszky et al., "The pharmacology of quinazolone derivatives." *Acta Physiologica XXVII*, 81–90 (1964).

Gujral et al., "Evaluation of anticonvulsant activity of 2,3–Disubstituted quinazolones: a new class of anticonvulsant drugs." *Ind. J. Med. Res.*, 45(2):207–211 (1957).

Brown and Goenechea, "Methaqualone: metabolic kinetic, and clinical pharmacologic observations." *Clinical Pharmacology and Therapeutics*, 14(3):314–324.

Ager et al., "Synthesis and central nervous system activity of quinazolones related to 2–methyl–3–(o–tolyl)–4–(3H)–quinazolone (Methaqualone)." *J. of Med. Chem.*, 20(3):379–386 (1977).

Weaver et al., Some central nervous system depressant properties of 2–methyl–3–o–tlyl–4(3H)–quinazolinone (TR–495) ($^1$), *Biomedical Research Dept. Pitman–Moore Co., Division of the Dow Chemical Company*, 119–1216 (1962).

Seth et al., "Effect of 2–methyl–3– ortho–tolyl–4–quinazolone on the oxidation of pyruvic acid in brain." *Biochem. Pharm.*, 13:1362–1363 (1964).

Bianchi and David, "The anticonvulsant properties of 2–methyl–3–p–bromophenyl–3H–4–quinazolone hydrochloride (B.D.H. 1880) and some related compounds." *Biological Laboratories, The British Drug Houses, Ltd.*, (1960).

Smith and Atigada, "Condensation of homophthalic anhydrides with heterocyclic imines and DMAD under mild conditions." *J. Heterocyclic Chem.*, 28:1813–1815 (1991).

Cushman and Castagnoli, "The condensation of succinic anhydrides with schiff bases. Scope and mechanism." *J. Org. Chem.*, 36(22):3404–3406 (1971).

Castagnoli Neal, "The condensation of succinic anhydride with benzylidinemethylamine. A stereo selective synthesis of trans–and cis–1–methyl–4–carboxy– 5–phenyl– 2–pyrrolidinone." *J. Org. Chem.*, 34(10):3187–3189 (1969).

(List continued on next page.)

*Primary Examiner*—Ponnathapura Achutamurthy
*Assistant Examiner*—Padmashri Ponnaluri
*Attorney, Agent, or Firm*—Campbell & Flores LLP

[57] ABSTRACT

The present invention provides synthetic combinatorial libraries of organic compounds based on the quinazolinone ring.

14 Claims, No Drawings

OTHER PUBLICATIONS

Cushman and Castagnoli, "The synthesis of trans-3'-methylnicotine." *J. Org. Chem.*, 37(8):1268–1271 (1972).

Cushman and Castagnoli, "Synthesis of pharmacologically active nitrogen analogs of the tetrahydrocannabinols." *J. Org. Chem.*, 39(11):1546–1550 (1974).

Cushman and Madaj, "A Study and mechanistic interpretation of the electronic and steric effects that determine the stereochemical outcome of the reaction of schiff bases with homophthalic anhydride and a 3–phenylsuccinic anhydride." *J. Org. Chem.*, 52:907–915 (1987).

Cushman and Castagnoli, "A novel approach to the synthesis of nitrogen analogs of the tetrahydrocannabinols." *J. Org. Chem.*, 38(3):440–448 (1973).

Chiele and Fregnan, "Inhibition of conditioned avoidance response by a new neuroleptic (LR 511). Interference with drugs endowed with different CNA activity." *Pharm. Research Comm.*, 11(7):617–621 (1979).

Tamura et al., "Cycloaddition of homophthalic anhydride: A new and simple route to linearly condensed phenolic compounds." *Tetrahedron Letters*, 22(43):4283–4286 (1981).

Wenker, Henry, "Syntheses from ethanolamine. V. Synthesis of $\Delta^2$–Oxazoline and of 2.2'–$\Delta^2$–Di–oxazoline." *J. of Am. Chem. Society*, 60(8):2152–2153 (1938).

Smith et al., "Synthetic approaches to hexahydropyrrolo[1, 2-b]isoquinolones." *J. Heterocyclic Chem.*, 26:1815–1817 (1989).

Coppola, Gary "Novel heterocycles. 8. Fused isoquinolines derived from the reaction of homophthalic anhydride with cyclic imino ethers." *J. Heterocyclic Chem.*, 18:767–770 (1981).

Haimova et al., "A highly stereoselective synthesis of 3,4–dihydro–1(2H)–isoquinolinones and 8–oxoberbines from homophthalic anhydrides and azomethines." *Tetrahedron*, 33:331–336 (1977).

Tamura et al., "Strong base induced cycloaddition of homophthalic anhydrides leading to peri–hydroxy polycyclic compounds." *J. Org. Chem.*, 49:473–478 (1984).

Harrison and Smith, "The synthesis of some cyclic hydroxamic acids from 0–aminocarboxylic acids." *J. Chem. Soc.*, 2157–2160 (1960).

Okumura et al., "4–Oxo–1,2,3,4–tetrahydroquinazolines. I. Syntheses and pharmacological properties of 2–methyl–3–aryl–4–oxo–1,2,3,4–tetrahydroquinazolines and their 1–acyl derivatives." *J. Mednl. Pharm. Chem.*, 11:348–352 (1968).

Chappell and Seemann, "Antitussive drugs." In: *Progress in Medicinal Chemistry*, Elseveir Science Publishers, Amsterdam., 89–145 (1963).

SYNTHESIS OF QUINAZOLINONE LIBRARIES AND DERIVATIVES THEREOF

This application claims the benefit of U.S. provisional application No. 60/031,090, filed Sep. 15, 1995, which was converted from U.S. Ser. No. 08/529,404, now abandoned.

BACKGROUND OF THE INVENTION

1. Field of the Invention

The present invention relates generally to the field of synthetic combinatorial libraries and, more specifically, to the generation of libraries of small organic compounds based on the quinazolinone ring.

2. Background Information

Interest in the medicinal chemistry of quinazoline derivatives was stimulated in the early 1950's with the elucidation of a quinazoline alkaloid, 3-[β-keto-γ(3-hydroxy-2-piperidyl)-propyl]-4-quinazolone, from an Asian plant known for its antimalarial properties. In a quest to find additional antimalarial agents, various substituted quinazolines have been synthesized. Of particular import was the synthesis of the derivative 2-methyl-3-o-tolyl-4-(3H)-quinazolinone. This compound, known by the name methaqualone, though ineffective against protozoa, was found to be a potent hypnotic.

Since the introduction of methaqualone and its discovery as a hypnotic, the pharmacological activity of quinazolinones, and related compounds, has been investigated. Quinazolinones and derivatives thereof are now known to have a wide variety of biological properties, including hypnotic, sedative, analgesic, anticonvulsant, antitussive and anti-inflammatory effects.

The classical organic synthesis of variously substituted quinazolinones is known. For example, as described in Ager et al., *J. of Med. Chem.*, 20:379–386 (1977), quinazolinones can be obtained by acid-catalyzed condensation of N-acylanthranilic acids with aromatic primary amines. However, the current synthesis and study of quinazolinones is a slow process. Each quinazolinone must be individually synthesized and separately tested. There exists a need to more efficiently synthesize and test various quinazolinones.

During the past four years there has been substantial development of chemically synthesized combinatorial libraries (SCLs) made up of peptides. The preparation and use of synthetic peptide combinatorial libraries has been described, for example, in Houghten et al., Nature 354, 84 (1991). Such SCLs provide the efficient synthesis of an extraordinary number of various peptides and screening of the library rapidly identifies lead pharmaceutical compounds. Combinatorial approaches have recently been extended to "organic," or non-peptidic libraries, as described, for example, in Gordon et al., *J. Med. Chem.*, 37:1385–1401 (1994). The organic libraries to present date, however, are of limited diversity and generally relate to peptidomimetic compounds; in other words, organic molecules that retain peptide chain pharmacophore groups similar to those present in the corresponding peptide. There exists a need to develop more complex "organic" libraries based on heterocyclic medicinal compounds which would require less optimization, synthesis, modification, and testing to bring an organic pharmaceutical product to fruition. In particular, such organic libraries are needed to prepare and screen quinazolinones and derivatives thereof. This invention satisfies these needs and provides related advantages as well.

SUMMARY OF THE INVENTION

The present invention relates to the generation of synthetic combinatorial libraries of organic compounds based on the quinazolinone ring of the formula:

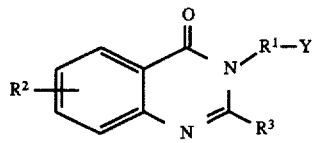

wherein $R^1$, $R^2$, $R^3$, and Y have the meanings provided below.

DETAILED DESCRIPTION OF THE INVENTION

The present invention provides a library of five or more variously substituted quinazolinones wherein each quinazolinone contained within the mixture has the basic ring structure of Formula I:

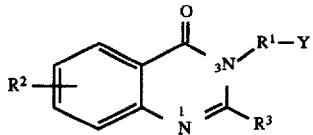

In the above Formula I:

$R^1$ is a hydrogen atom, $C_1$ to $C_6$ alkyl; $C_1$ to $C_6$ substituted alkyl, $C_7$ to $C_{12}$ phenylalkyl, $C_7$ to $C_{12}$ substituted phenylalkyl, phenyl, substituted phenyl, $C_3$ to $C_7$ cycloalkyl, or $C_3$ to $C_7$ substituted cycloalkyl;

$R^2$ is a hydrogen atom, halo, hydroxy, protected hydroxy, cyano, nitro, $C_1$ to $C_6$ alkyl, $C_2$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_1$ to $C_4$ alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_3$ to $C_7$ cycloalkenyl, $C_3$ to $C_7$ substituted cycloalkenyl, a heterocyclic ring, $C_7$ to $C_{12}$ phenylalkyl, $C_7$ to $C_{12}$ substituted phenylalkyl, phenyl, substituted phenyl, cyclic $C_2$ to $C_{10}$ alkylene, substituted cyclic $C_2$ to $C_{10}$ alkylene, cyclic $C_2$ to $C_{10}$ heteroalkylene, substituted cyclic $C_2$ to $C_{10}$ heteroalkylene, carboxy, protected carboxy, hydroxymethyl, protected hydroxymethyl, (monosubstituted)amino, protected (monosubstituted) amino, (disubstituted) amino, carboxamide, protected carboxamide, $C_1$ to $C_4$ alkylthio, $C_1$ to $C_4$ alkylsulfonyl, methylsulfonylamino, $C_1$ to $C_4$ alkylsulfoxide, phenylthio, substituted phenylthio, phenylsulfoxide, substituted phenylsulfoxide, phenylsulfonyl, or substituted phenylsulfonyl;

$R^3$ is $C_1$ to $C_6$ alkyl, $C_2$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_3$ to $C_7$ cycloalkyl, $C_3$ to $C_7$ substituted cycloalkyl, $C_7$ to $C_{12}$ phenylalkyl, $C_7$ to $C_{12}$ substituted phenylalkyl, phenyl, or substituted phenyl; and Y may be absent and, if present, is carboxylic acid, carboxamide, protected carboxamide, an amino resin, a hydroxy resin, methylamine, or N-alkylated methylamine.

In one embodiment of the above quinazolinone library, $R^1$ is n-prop-1,3-yl, n-prop-1,1-yl, n-pent-1,5-yl, n-hex-1,6-yl, p-benzyl, 2-chloro-p-phenyl, p-phenyl, 2-methyl-m-phenyl, 2-hydroxy-p-phenyl, and 2-(phenyl)-n-prop-1,3-yl, or the α-carbon and side chain of an amino acid and more preferably the α-carbon and side chain of an amino acid as provided in Table I.

TABLE I

| Amino Acid | R$^1$ |
|---|---|
| Glycine | —CH$_2$— |
| Alanine | —CH(CH$_3$)— |
| Valine | —CH(CH(CH$_3$)$_2$)— |
| Leucine | —CH(CH$_2$CH(CH$_3$)$_2$)— |
| Isoleucine | —CH(CH(CH$_3$)CH$_2$CH$_3$)— |
| Arginine | —CH(CH$_2$CH$_2$CH$_2$NHCNHNH$_2$)— |
| Serine | —CH(CH$_2$OH)— |
| Threonine | —CH(CH(OH)CH$_3$)— |
| Phenylalanine | 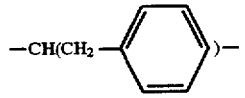 |
| Tyrosine | 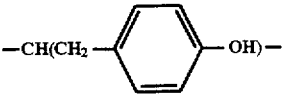 |
| β-Alanine | —CH$_2$—CH$_2$— |
| Norvaline | —CH(CH$_2$CH$_2$CH$_3$)— |
| Norleucine | —(CH(CH$_2$CH$_2$CH$_2$CH$_3$)— |
| Naphthylalanine | 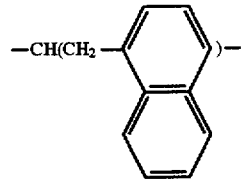 |

Also in the embodiment of the above quinazolinone library of Formula I, R$^2$ is a hydrogen atom, 6,8-dimethyl, 6-hydroxy, a 1,4-butadienyl moiety such that a naphthyl ring results, or halo, and more preferably 6,7-difluoro, 6,8-dichloro, or 6,8-dibromo; R$^3$ is methyl; and Y may be present or absent and, if present, is selected from the group consisting of carboxylic acid, carboxamide, protected carboxamide, an amino resin, or a hydroxy resin.

In an alternative embodiment of the quinazolinone library, R$^1$ is the α-carbon and corresponding side chain of an amino acid as provided in Table II.

TABLE II

| Amino Acid | R$^1$ |
|---|---|
| Glycine | —CH$_2$— |
| Alanine | —CH(CH$_3$)— |
| Valine | —CH(CH(CH$_3$)$_2$)— |
| Leucine | —CH(CH$_2$CH(CH$_3$)$_2$)— |
| Isoleucine | —CH(CH(CH$_3$)CH$_2$CH$_3$)— |
| Lysine | —CH((CH$_2$)$_4$NH$_2$)— |
| Arginine | —CH(CH$_2$CH$_2$CH$_2$NHCNHNH$_2$)— |
| Glutamic Acid | —CH(CH$_2$CH$_2$COOH)— |
| Serine | —CH(CH$_2$OH)— |
| Threonine | —CH(CH(OH)CH$_3$)— |
| Phenylalanine | 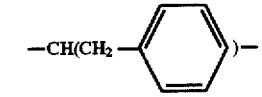 |

TABLE II-continued

| Amino Acid | R$^1$ |
|---|---|
| p-Chlorophenylalanine | 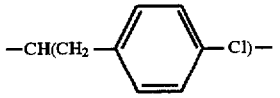 |
| p-Flurophenylalanine | 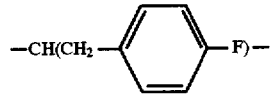 |
| p-Iodophenylalanine | 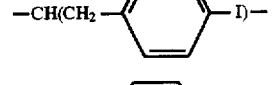 |
| Tyrosine |  |
| O-Ethyl tyrosine |  |
| Trypthophan | 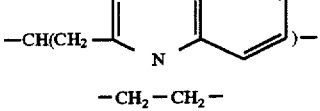 |
| β-Alanine | —CH$_2$—CH$_2$— |
| Norvaline | —CH(CH$_2$CH$_2$CH$_3$)— |
| Norleucine | —(CH(CH$_2$CH$_2$CH$_2$CH$_3$)— |
| Napthylalanine | 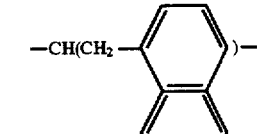 |
| Cyclohexylalanine | 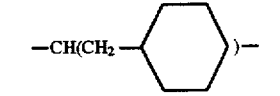 |
| β-Thienylalanine | 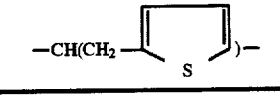 |

Also in this alternative embodiment, R$^2$ is a hydrogen atom, 6,8-dimethyl, a 1,4-butadienyl moiety such that a naphthyl ring results, 8-hydroxy, 8-methoxy, 8-methyl, 6-methyl, or halo, and more preferably 7,8-difluoro, 5,6,7,8-tetrafluoro, 7-chloro, 7-fluoro, or 6-halo, wherein halo is fluoro, chloro, bromo, or iodo; R$^3$ is methyl; and Y may be present or absent, and if present, is selected from the group consisting of carboxylic acid, carboxamide, protected carboxamide, an amino resin, or a hydroxy resin.

The present invention also provides libraries of various quinazolinone derivatives. Once the initial quinazolinone structure of Formula I is prepared by any one of the above described methods the quinazolinone mixture can be further chemically transformed to extend the range and chemical diversity of the compounds. Using the "libraries from libraries" concept, as described in Ostresh et al., *Proc. Natl. Acad. Sci.*, 91:11138–11142 (1994), various libraries of quinazolinone derivatives can be prepared by chemically altering the initial quinazolinone library.

Such quinazolinone derivative libraries can be made by modifying the above described quinazolinone library in a variety of ways. For example, the above quinazolinone library can be modified to yield N-styryl derivatives of quinazolinones. Therefore, the present invention provides a mixture of five or more quinazolinone derivatives of the structure of Formula II:

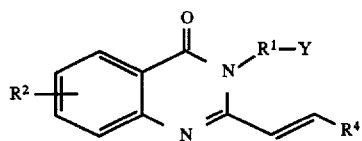

In the above Formula II, $R^1$, $R^2$, and Y have the same meaning as provided above and $R^4$ is as follows:

$R^4$ is $C_1$ to $C_6$ alkyl; $C_1$ to $C_6$ substituted alkyl, $C_7$ to $C_{12}$ phenylalkyl, $C_7$ to $C_{12}$ substituted phenylalkyl, phenyl, substituted phenyl, naphthyl, substituted naphthyl, or a heterocyclic ring, or a cyclic $C_2$ to $C_{10}$ heteroalkylene.

In one embodiment of the styryl derivatives of quinazolinone, $R^1$ is n-prop-1,3-yl, n-prop-1,1-yl, n-pent-1, 5-yl, n-hex-1,6-yl, p-benzyl, 2-chloro-p-phenyl, p-phenyl, 2-methyl-m-phenyl, 2-hydroxy-p-phenyl, and 2-(phenyl)-n-prop-1,3-yl, or the α-carbon and side chain of an amino acid and more preferably the α-carbon and side chain of an amino acid as provided in Table I above; $R^2$ is a hydrogen atom, 6,8-dimethyl, 6-hydroxy, 1,4-butadienyl moiety such that a naphthyl ring results, or halo, and more preferably 6,7-difluoro, 6,8-dichloro, or 6,8-dibromo; $R^4$ is phenyl, 2,4-dichlorophenyl, 2-naphthyl, 2,5-dimethylphenyl, 3,4-difluorophenyl, 4-bromophenyl, 3-(4-methylphenoxy)phenyl, 4-methoxyphenyl, biphenyl, 6-methyl-pyridin-2-yl, 2-(methoxy)-naphthyl, 2,4,5,-trimethoxyphenyl, or 4-(dimethylamino)phenyl; and Y may be present or absent and, if present, is carboxylic acid, carboxamide, protected carboxamide, an amino resin, or a hydroxy resin.

In an alternative embodiment of the styryl derivatives of quinazolinone, $R^1$ is the α-carbon and corresponding side chain of an amino acid as provided in Table II.

TABLE II

| Amino Acid | $R^1$ |
|---|---|
| Glycine | —$CH_2$— |
| Alanine | —$CH(CH_3)$— |
| Valine | —$CH(CH(CH_3)_2)$— |
| Leucine | —$CH(CH_2CH(CH_3)_2)$— |
| Isoleucine | —$CH(CH(CH_3)CH_2CH_3)$— |
| Lysine | —$CH((CH_2)_4NH_2)$— |
| Arginine | —$CH(CH_2CH_2CH_2NHCNHNH_2)$— |
| Glutamic Acid | —$CH(CH_2CH_2COOH)$— |
| Serine | —$CH(CH_2OH)$— |
| Threonine | —$CH(CH(OH)CH_3)$— |
| Phenylalanine | —CH(CH₂—⟨phenyl⟩)— |
| p-Chlorophenylalanine | —CH(CH₂—⟨phenyl⟩—Cl)— |
| p-Flurophenylalanine | —CH(CH₂—⟨phenyl⟩—F)— |

TABLE II-continued

| Amino Acid | $R^1$ |
|---|---|
| p-Iodophenylalanine | —CH(CH₂—⟨phenyl⟩—I)— |
| Tyrosine | —CH(CH₂—⟨phenyl⟩—OH)— |
| O-Ethyl tyrosine | —CH(CH₂—⟨phenyl⟩—OEt)— |
| Trypthophan | —CH(CH₂—⟨indole⟩)— |
| β-Alanine | —$CH_2$—$CH_2$— |
| Norvaline | —$CH(CH_2CH_2CH_3)$— |
| Norleucine | —$(CH(CH_2CH_2CH_2CH_3))$— |
| Napthylalanine | —CH(CH₂—⟨naphthyl⟩)— |
| Cyclohexylalanine | —CH(CH₂—⟨cyclohexyl⟩)— |
| β-Thienlalanine | —CH(CH₂—⟨thienyl⟩)— |

Also in this alternative embodiment, $R^2$ is a hydrogen atom, 6,8-dimethyl, a 1,4-butadienyl moiety such that a naphthyl ring results, 8-hydroxy, 8-methoxy, 8-methyl, 6-methyl, or halo, and more preferably 7,8-difluoro, 5,6,7, 8-tetrafluoro, 7-chloro, 7-fluoro, or 6-halo, wherein halo is fluoro, chloro, bromo, or iodo; $R^4$ phenyl, 2-bromophenyl, 2-fluorophenyl, 2-methoxyphenyl, 3-bromophenyl, 3-cyanophenyl, 3-fluorophenyl, 3-methoxyphenyl, 3-methylphenyl, 3-(trifluoromethyl)phenyl, 4-bromophenyl, 4-cyanophenyl, 4-fluorophenyl, 4-(dimethylamino)phenyl, 4-isopropylphenyl, 4-methoxyphenyl, 4-methylbenzoate, 4-(methylthio)phenyl, 4-propoxyphenyl, 4-(trifluoromethyl) phenyl, 3,5-dimethoxyphenyl, 2,3-difluorophenyl, 2,5-dimethylphenyl, 2,4-dichlorophenyl, 2-chloro-6-fluorophenyl, 3-bromo-4-fluorophenyl, 3,4-dibenzyloxyphenyl, 3,4-dichlorophenyl, 3,4-difluorophenyl, 3-fluoro-4-methoxyphenyl, 3-methyl-4-methoxyphenyl, 2,3,5-trichlorophenyl, 2,4,5-trimethoxyphenyl, 1,4-phenyldioxan-6-yl, 3,4-(methylenedioxy)phenyl, 3-(4-methylphenoxy)phenyl, 3-(3,4-dichlorophenoxy)phenyl, 3-(3,4-methoxyphenoxy)phenyl, 4-phenoxyphenyl, 3-phenoxyphenyl, biphenyl, 1-naphthyl, 2-naphthyl, 2-(methoxy)-naphthyl, 4-(methoxy)-naphthyl, 9-ethyl-3-carbozoyl, thiofuranyl, 5-methyl-thiofuran-2-yl, furan-2-yl, furan-3-yl, 5-methyl-furan-2-yl, pyridin-3-yl, pyridin-4-yl, 6-methyl-pyridin-2-yl, 1-methyl-pyrrol-2-yl, 1-methylindo- 3-yl, 2,6-dichlorophenyl, 2,3,4-trimethoxyphenyl, 2,3-dimethyl-4-methoxyphenyl, 2,4-dimethoxy-3-methylphenyl, 2,5-dimethyl-4-methoxyphenyl, 2-ethoxyphenyl, 3-(trifluoromethyl)phenoxyphenyl, 3-(4-t-butylphenoxy)phenyl, 4-(3-dimethylaminopropoxy) phenyl, 5-bromo-thiofuran-2-yl, 4-benzyloxy-3-methoxyphenyl, or 4-stilbenephenyl; and Y may be present or absent, and if present, is selected from the group consisting of carboxylic acid, carboxamide, protected carboxamide, an amino resin, or a hydroxy resin.

Another library containing five or more quinazolinone derivatives provided by the present invention include 1,2-dihydro derivatives having the structure of Formula III:

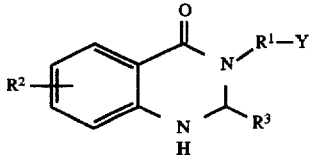

In Formula III, $R^1$, $R^2$, $R^3$, and Y have the same meanings as provided above.

In yet another embodiment of the present invention, the basic ring nitrogen at position 1 can be alkylated using a variety of alkylating agents to prepare a mixture of five or more quinazolinone derivatives of the following Formula IV:

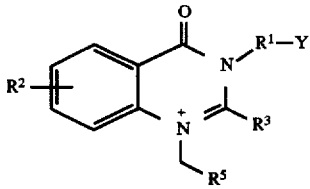

In Formula IV, $R^1$, $R^2$, $R^3$, and Y are as defined above, and $R^5$ is $C_1$ to $C_6$ alkyl; $C_1$ to $C_6$ substituted alkyl, $C_1$ to $C_4$ alkoxy, $C_7$ to $C_{12}$ phenylalkyl, $C_7$ to $C_{12}$ substituted phenylalkyl, phenyl, or substituted phenyl.

Also provided by the present invention is a library of five or more quinazolinone derivatives having the structure of Formula V:

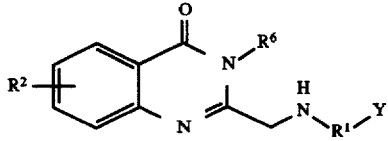

The substituents $R^1$, $R^2$, and Y In Formula V are identical to those defined above with respect to Formula I. The substituent $R^6$ a hydrogen atom, $C_1$ to $C_6$ alkyl; $C_1$ to $C_6$ substituted alkyl, $C_7$ to $C_{12}$ phenylalkyl, $C_7$ to $C_{12}$ substituted phenylalkyl, phenyl, substituted phenyl, $C_3$ to $C_7$ cycloalkyl, $C_3$ to $C_7$ substituted cycloalkyl, carboxylic acid, carboxamide, or protected carboxamide.

In the above Formulae the stereochemistry of the chiral $R^1$ through $R^6$ groups can independently be in the R or S configuration, or a mixture of the two.

In the above Formulae, the term "$C_1$ to $C_6$ alkyl" denotes such radicals as methyl, ethyl, n-propyl, isopropyl, n-butyl, sec-butyl, tert-butyl, amyl, tert-amyl, hexyl and the like. The preferred "$C_1$ to $C_6$ alkyl" group is methyl.

The term "$C_2$ to $C_7$ alkenyl" denotes such radicals as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, as well as dienes and trienes of straight and branched chains.

The term "$C_2$ to $C_7$ alkynyl" denotes such radicals as ethynyl, propenyl, butynyl, pentynyl, hexynyl, heptynyl, as well as di- and tri-ynes.

The term "$C_1$ to $C_6$ substituted alkyl," "$C_2$ to $C_7$ substituted alkenyl," and "$C_2$ to $C_7$ substituted alkynyl," denotes that the above $C_1$ to $C_6$ alkyl groups and $C_2$ to $C_7$ alkenyl and alkynyl groups are substituted by one or more, and preferably one or two, halogen, hydroxy, protected hydroxy, cyclohexyl, naphthyl, thiofuranyl, indolyl, amino, protected amino, (monosubstituted)amino, protected (monosubstituted)amino, (disubstituted)amino, guanidino, imidazolyl, indolyl, pyrolidinyl, $C_1$ to $C_7$ acyloxy, nitro, $C_1$ to $C_4$ alkyl ester, carboxy, protected carboxy, carbamoyl, carbamoyloxy, carboxamide, protected carboxamide, cyano, methylsulfonylamino, sulfurhydryl, $C_1$ to $C_4$ alkylthio, $C_1$ to $C_4$ alkyl sulfonyl or $C_1$ to $C_4$ alkoxy groups. The substituted alkyl groups may be substituted once or more, and preferably once or twice, with the same or with different substituents.

Examples of the above substituted alkyl groups include the cyanomethyl, nitromethyl, chloromethyl, hydroxymethyl, tetrahydropyranyloxymethyl, trityloxymethyl, propionyloxymethyl, aminomethyl, carboxymethyl, allyloxycarbonylmethyl, allylcaroxybonylaminomethyl, carbamoyloxymethyl, methoxymethyl, ethoxymethyl, t-butoxymethyl, acetoxymethyl, chloromethyl, bromomethyl, iodomethyl, 6-hydroxyhexyl, 2,4-dichloro(n-butyl), 2-amino(isopropyl), 2-carbamoyloxyethyl chloroethyl, bromoethyl, fluoroethyl, iodoethyl, chloropropyl, bromopropyl, fluoropropyl, iodopropyl and the like.

The term "$C_1$ to $C_4$ alkoxy" as used herein denotes groups such as methoxy, ethoxy, n-propoxy, isopropoxy, n-butoxy, t-butoxy and like groups. A preferred $C_1$ to $C_4$ alkoxy group is methoxy.

The term "$C_1$ to $C_7$ acyloxy" denotes herein groups such as formyloxy, acetoxy, propionyloxy, butyryloxy, pentanoyloxy, hexanoyloxy, heptanoyloxy, and the like.

Similarly, the term "$C_1$ to $C_7$ acyl" encompasses groups such as formyl, acetyl, propionyl, butyryl, pentanoyl, hexanoyl, heptanoyl, benzoyl and the like.

The substituent term "$C_3$ to $C_7$ cycloalkyl" includes the cyclopropyl, cyclobutyl, cyclopentyl, cyclohexyl or cycloheptyl rings. The substituent term "$C_3$ to $C_7$ substituted cycloalkyl" indicates the above cycloalkyl rings substituted by a halogen, hydroxy, protected hydroxy, $C_1$ to $C_6$ alkyl, $C_1$ to $C_4$ alkoxy, carboxy, protected carboxy, amino, or protected amino.

The substituent term "$C_3$ to $C_7$ cycloalkenyl" indicates a 1,2, or 3-cyclopentenyl ring, a 1,2,3 or 4-cyclohexenyl ring or a 1,2,3,4 or 5-cycloheptenyl ring, while the term "substituted $C_3$ to $C_7$ cycloalkenyl" denotes the above $C_3$ to $C_7$ cycloalkenyl rings substituted by a $C_1$ to $C_6$ alkyl radical, halogen, hydroxy, protected hydroxy, $C_1$ to $C_4$ alkoxy, carboxy, protected carboxy, amino, or protected amino.

The term "heterocyclic ring" denotes optionally substituted five-membered or six-membered rings that have 1 to 4 heteroatoms, such as oxygen, sulfur and/or nitrogen, in particular nitrogen, either alone or in conjunction with sulfur or oxygen ring atoms. These five-membered or six-membered rings may be fully unsaturated or partially unsaturated, with fully unsaturated rings being preferred. Preferred heterocyclic rings include pyridino, pyrimidino, and pyrazino, furano, and thiofurano rings.

The term "$C_7$ to $C_{12}$ phenylalkyl" denotes a $C_1$ to $C_6$ alkyl group substituted at any position by a phenyl ring. Examples of such a group include benzyl, 2-phenylethyl, 3-phenyl-(n-prop-1-yl), 4-phenyl-(-hex-1-yl), 3-phenyl-(n-am-2-yl), 3-phenyl-(sec-butyl), and the like. A preferred group is the benzyl group.

The term "$C_7$ to $C_{12}$ substituted phenylalkyl" denotes a $C_7$ to $C_{12}$ arylalkyl group substituted on the $C_1$ to $C_6$ alkyl portion with one or more, and preferably one or two, groups chosen from halogen, hydroxy, protected hydroxy, keto, $C_2$ to $C_3$ cyclic ketal, amino, protected amino, $C_1$ to $C_7$ acyloxy, nitro, carboxy, protected carboxy, carbamoyl, carbamoyloxy, cyano, N-(methylsulfonylamino) or $C_1$ to $C_4$ alkoxy; and/or the phenyl group may be substituted with 1 or 2 groups chosen from halogen, hydroxy, protected hydroxy, nitro, $C_1$ to $C_6$ to alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, a N-(methylsulfonylamino) group, or a phenyl group, substituted or unsubstituted, for a resulting biphenyl group When either the $C_1$ to $C_6$ alkyl portion or the phenyl portion or both are mono- or di-substituted the substituents can be the same or different.

Examples of the term "$C_7$ to $C_{12}$ substituted phenylalkyl" include groups such as 2-phenyl-1-chloroethyl, 2-(4-methoxyphenyl)eth-1-yl, 2,6-dihydroxy-4-phenyl(n-hex-2-yl), 5-cyano-3-methoxy-2-phenyl(n-pent-3-yl), 3-(2,6-dimethylphenyl)n-prop-1-yl, 4-chloro-3-aminobenzyl, 6-(4-methoxyphenyl)-3-carboxy(n-hex-1-yl), 5-(4-aminomethylphenyl)-3-(aminomethyl)(n-pent-2-yl), 5-phenyl-3-keto-(n-pent-1-yl), 4-(4-aminophenyl)-4-(1,4-oxetanyl)(n-but-1-yl), and the like.

The term "substituted phenyl" specifies a phenyl group substituted with one or more, and preferably one or two, moieties chosen from the groups consisting of halogen, hydroxy, protected hydroxy, cyano, nitro, $C_1$ to $C_6$ alkyl, $C_1$ to $C_6$ substituted alkyl, $C_1$ to $C_4$ alkoxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, trifluoromethyl, N-(methylsulfonylamino), or phenyl, substituted or unsubstituted, such that, for example, a biphenyl results.

Examples of the term "substituted phenyl" includes a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono or di(hydroxy)phenyl groups such as 4-hydroxyphenyl, 3-hydroxyphenyl, 2,4-dihydroxyphenyl, the protected-hydroxy derivatives thereof and the like; a nitrophenyl group such as 3-or 4-nitrophenyl; a cyanophenyl group for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-prop-1-yl)phenyl and the like; a mono or di(alkoxyl)phenyl group, for example, 2,6-dimethoxyphenyl, 4-methoxyphenyl, 3-ethoxyphenyl, 4-(isopropoxy)phenyl, 4-(t-butoxy)phenyl, 3-ethoxy-4-methoxyphenyl, 3-(4-methylphenoxy)phenyl, and the like,; 3-or 4-trifluoromethylphenyl; a mono- or dicarboxyphenyl or (protected carboxy)phenyl group such as 4-carboxyphenyl or 2,4-di(protected carboxy)phenyl; a mono-or di(hydroxymethyl)phenyl or (protected hydroxymethyl) phenyl such as 3-(protected hydroxymethyl)phenyl or 3,4-di(hydroxymethyl)phenyl; a mono- or di(aminomethyl) phenyl or (protected aminomethyl)phenyl such as 2-(aminomethyl)phenyl or 2,4-(protected aminomethyl) phenyl; or a mono- or di(N-(methylsulfonylamino))phenyl such as 3-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy 4-chlorophenyl and the like.

The term "substituted naphthyl" specifies a naphthyl group substituted with one or more, and preferably one or two, moieties chosen from the groups consisting of halogen, hydroxy, protected hydroxy, cyano, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, amino, protected amino,(monosubstituted) amino, protected (monosubstituted)amino, (disubstituted) amino trifluoromethyl or N-(methylsulfonylamino). Examples of substituted naphthyl include 2-(methoxy)-naphthyl and 4-(methoxy)naphthyl.

The terms "halo" and "halogen" refer to the fluoro, chloro, bromo or iodo groups.

The term "(monosubstituted)amino" refers to an amino group with one substituent chosen from the groups consisting of phenyl, substituted phenyl, $C_1$ to $C_6$ alkyl, and $C_7$ to $C_{12}$ arylalkyl, wherein the latter three substituent terms are as defined above. The (monosubstituted)amino can additionally have an amino-protecting group as encompassed by the term "protected (monosubstituted)amino."

The term "(disubstituted)amino" refers to amino groups with two substituents chosen from the group consisting of phenyl, substituted phenyl, $C_1$ to $C_6$ alkyl, and $C_7$ to $C_{12}$ arylalkyl wherein the latter three substituent terms are as described above. The two substituents can be the same or different.

The term "amino-protecting group" as used herein refers to substituents of the amino group commonly employed to block or protect the amino functionality while reacting other functional groups on the amine component. The term "protected (monosubstituted)amino" means there is an amino-protecting group on the monosubstituted amino nitrogen atom. In addition, the term "protected carboxamide" means there is an amino-protecting group replacing the proton so that there is no N-alkylation. Examples of such amino-protecting groups include the formyl ("For") group, the trityl group, the phthalimido group, the trichloroacetyl group, the chloroacetyl, bromoacetyl, and iodoacetyl groups, urethane-type blocking groups, such as t-butoxy-carbonyl ("Boc"), 2-(4-biphenylyl)propyl(2)oxycarbonyl ("Bpoc"), 2-phenylpropyl(2)oxycarbonyl ("Poc"), 2-(4-xenyl) isopropoxycarbonyl, 1,1-diphenylethyl(1)-oxycarbonyl, 1,1-diphenylpropyl(1)oxycarbonyl, 2-(3,5-dimethoxyphenyl)propyl(2)oxycarbonyl ("Ddz"), 2-(p-toluyl)propyl(2)oxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl) ethoxycarbonyl, 2-(methylsulfonyl)ethoxycarbonyl, 2-(triphenylphosphino)-ethoxycarbonyl, 9-fluoroenylmethoxycarbonyl ("Fmoc"), 2-(trimethylsilyl) ethoxycarbonyl, allyloxycarbonyl, 1-(trimethylsilylmethyl) prop-1-enyloxycarbonyl, 5-benz-isoxalylmethoxycarbonyl, 4-acetoxybenzyloxycarbonyl, 2,2,2-trichloroethoxycarbonyl, 2-ethynyl(2)propoxy-carbonyl, cyclopropylmethoxycarbonyl, isobornyl-oxycarbonyl, 1-piperidyloxycarbonyl, benzyloxycarbonyl ("Z"), 4-phenylbenzyloxycarbonyl, 2-methylbenzyloxy-carbonyl, α-2,4,5,-tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy) benzyloxycarbonyl, and the like; the benzoylmethylsulfonyl group, dithiasuccinoyl ("Dts"), the 2-(nitro)phenylsulfenyl group ("Nps"), the diphenyl-phosphine oxide group, and like amino-protecting groups. The species of amino-protecting group employed is not critical so long as the derivatized amino group is stable to the conditions of the subsequent reaction(s) and can be removed at the appropriate point without disrupting the remainder of the compounds. Preferred amino-protecting groups are Boc and Fmoc. Further examples of amino-protecting groups embraced to by the above term are well known in organic synthesis and the peptide art and are described by, for example, T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, each of which is incorporated herein by reference. The related term "protected amino" defines an amino group substituted with an amino-protecting group discussed above.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-timethoxytrityl, 2-phenylprop-2-yl, trimethylsilyl, t-butyldimethylsilyl, 2,2,2-trichloroethyl, β-(trimethylsilyl) ethyl, β-(di(n-butyl)methylsilyl)ethyl, p-toluenesulfonylethyl, 4-nitrobenzyl-sulfonylethyl, allyl, cinnamyl, 1-(trimethylsilylmethyl)-prop-1-en-3-yl, and like moieties. The species of carboxy-protecting group employed is not critical so long as the derivatized carboxylic acid is stable to the conditions of subsequent reaction(s) and can be removed at the appropriate point without disrupting the remainder of the molecule. Further examples of these groups are found in E. Haslam, "Protective Groups in Organic Chemistry," J. G. W. McOmie, Ed., Plenum Press, New York, N.Y., 1973, Chapter 5, and T. W. Greene and P. G. M. Wuts, "Protective Groups in Organic Synthesis," 2nd ed., John Wiley and Sons, New York, N.Y., 1991, Chapter 5, each of which is incorporated herein by reference. A related term is "protected carboxy," which refers to a carboxy group substituted with one of the above carboxy-protecting groups.

The term "hydroxy-protecting group" refers to readily cleavable groups bonded to hydroxyl groups, such as the tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl and 2,2,2-trichloroethoxycarbonyl groups and the like. The species of hydroxy-protecting groups is not critical so long as the derivatized hydroxyl group is stable to the conditions of subsequent reaction(s) and can be removed at the appropriate point without disrupting the remainder of the quinazolinone molecule. Further examples of hydroxy-protecting groups are described by C. B. Reese and E. Haslam, "Protective Groups in Organic Chemistry,") J. G. W. McOmie, Ed., Plenum Press, New York, N.Y., 1973, Chapters 3 and 4, respectively, and T. W. Greene and P. G. M. Wuts, "Protective Groups in Organic Synthesis," 2nd ed., John Wiley and Sons, New York, N.Y., 1991, Chapters 2 and 3.

The substituent term "$C_1$ to $C_4$ alkylthio" refers to sulfide groups such as methylthio, ethylthio, n-propylthio, iso-propylthio, n-butylthio, t-butylthio and like groups.

The substituent term "$C_1$ to $C_4$ alkylsulfoxide" indicates sulfoxide groups such as methylsulfoxide, ethylsulfoxide, n-propylsulfoxide, iso-propylsulfoxide, n-butylsulfoxide, sec-butylsulfoxide, and the like.

The term "$C_1$ to $C_4$ alkylsulfonyl" encompasses groups such as methylsulfonyl, ethylsulfonyl, n-propylsulfonyl, iso-propylsulfonyl, n-butylsulfonyl, t-butylsulfonyl, and the like.

Phenylthio, phenyl sulfoxide, and phenylsulfonyl compounds are known in the art and these terms have their art recognized definition. By "substituted phenylthio," "substituted phenyl sulfoxide," and "substituted phenylsulfonyl" is meant that the phenyl can be substituted as described above in relation to "substituted phenyl."

The substituent terms "cyclic $C_2$ to $C_{10}$ alkylene," "substituted cyclic $C_2$ to $C_{10}$ alkylene," "cyclic $C_2$ to $C_{10}$ heteroalkylene," and "substituted cyclic $C_2$ to $C_{10}$ heteroalkylene," defines such a cyclic group bonded ("fused") to the phenyl radical. The cyclic group may be saturated or contain one or two double bonds. Furthermore, the cyclic group may have one or two methylene groups replaced by one or two oxygen, nitrogen or sulfur atoms.

The cyclic alkylene or heteroalkylene group may be substituted once or twice by substituents selected from the group consisting of the following moieties: hydroxy, protected hydroxy, carboxy, protected carboxy, keto, ketal, $C_1$ to $C_4$ alkoxycarbonyl, formyl, $C_2$ to $C_4$ alkanoyl, $C_1$ to $C_6$ alkyl, carbamoyl, $C_1$ to $C_4$ alkoxy, $C_1$ to $C_4$ alkylthio, $C_1$ to $C_4$ alkylsulfoxide, $C_1$ to $C_4$ alkylsulfonyl, halo, amino, protected amino, hydroxymethyl or a protected hydroxymethyl.

The cyclic alkylene or heteroalkylene group fused onto the benzene radical can contain two to ten ring members, but it preferably contains four to six members. Examples of such saturated cyclic groups are when the resultant bicyclic ring system is 2,3-dihydro-indanyl and a tetralin ring. When the cyclic groups are unsaturated, examples occur when the resultant bicyclic ring system is a naphthyl ring or indanyl. An example of a cyclic group which can be fused to a phenyl radical which has two oxygen atoms and which is fully saturated is dioxanyl. Examples of fused cyclic groups which each contain one oxygen atom and one or two double bonds are when the phenyl ring is fused to a furo, pyrano, dihydrofurano, or dihydropyrano ring. Examples of cyclic groups which each have one nitrogen atom and contain one or two double more double bonds are when the phenyl is fused to a pyridino or pyrano ring. An example of a fused ring system having one nitrogen and two phenyl radicals is a carbozoyl group. Examples of cyclic groups which each have one sulfur atom and contain one or two double bonds are when the phenyl is fused to a thieno, thiopyrano, dihydrothieno or dihydrothiopyrano ring. Examples of cyclic groups which contain two heteroatoms selected from sulfur and nitrogen and one or two double bonds are when the phenyl ring is fused to a thiazolo, isothiazolo, dihydrothiazolo or dihydroisothiazolo ring. Examples of cyclic groups which contain two heteroatoms selected from oxygen and nitrogen and one or two double bonds are when the benzene ring is fused to an oxazolo, isoxazolo, dihydrooxazolo or dihydroisoxazolo ring. Examples of cyclic groups which contain two nitrogen heteroatoms and one or two double bonds occur when the benzene ring is fused to a pyrazolo, imidazolo, dihydropyrazolo or dihydroimidazolo ring.

One or more of the quinazolinones or quinazolinone derivatives within a given library may be present as a pharmaceutically acceptable salt. The term "pharmaceutically-acceptable salt" encompasses those salts that form with the carboxylate anions and amine nitrogens and include salts formed with the organic and inorganic cations discussed below. Furthermore, the term includes salts that form by standard acid-base reactions with basic groups (such as amino groups) and organic or inorganic acids. Such acids include hydrochloric, sulfuric, phosphoric, acetic, succinic, citric lactic, maleic, fumaric, palmitic, cholic, pamoic, mucic, D-glutamic, d-camphoric, glutaric, phthalic, tartaric, lauric, stearic, salicyclic, methanesulfonic, benzenesulfonic, sorbic, picric, benzoic, cinnamic, and like acids.

The term "organic or inorganic cation" refers to counterions for the carboxylate anion of a carboxylate salt. The counter-ions are chosen from the alkali and alkaline earth metals, (such as lithium, sodium, potassium, barium and calcium); ammonium; and the organic cations (such as dibenzylammonium, benzylammonium, 2-hydroxyethylammonium, bis(2-hydroxyethyl)ammonium, phenylethylbenzylammonium, dibebenzylethylenediammonium, and like cations). Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is referred to by this term. For example, a cation for a carboxylate anion will exist when $R_2$ or $R_1$ is substituted with a (quaternary ammonium)methyl group. A preferred cation for the carboxylate anion is the sodium cation.

The compounds of the above Formulae can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

One or more quinazolinones or quinazolinone derivatives can be in the biologically active ester form, such as the non-toxic, metabolically-labile ester-form. Such ester forms induce increased blood levels and prolong the efficacy of the corresponding non-esterified forms of the compounds. Ester groups which can be used include the lower alkoxymethyl groups, for example, methoxymethyl, ethoxymethyl, iso-propoxymethyl and the like; the $\alpha$-($C_1$ to $C_4$) alkoxyethyl groups, for example methoxyethyl, ethoxyethyl, propxyethyl, iso-propoxyethyl, and the like; the 2-oxo-1,3-diosolen-4-ylmethyl groups, such as 5-methyl-2-oxo-1,3-dioxolen-4-ylmethyl, 5-phenyl-2-oxo-1,3-dioxolen-4-ylmethyl, and the like; the $C_1$ to $C_3$ alkylthiomethyl groups, for example methylthiomethyl, ethylthiomethyl, iso-propylthiomethyl, and the like; the acyloxymethyl groups, for example pivaloyloxymethyl, pivaloyloxyethyl, $\alpha$-acetoxymethyl, and the like; the ethoxycarbonyl-1-methyl group; the $\alpha$-acetoxyethyl; the 3-phthalidyl or 5,6-dimethylphthalidyl groups; the 1-($C_1$ to $C_4$ alkyloxycarbonyloxy)ethyl groups such as the 1-(ethoxycarbonyloxy)ethyl group; and the 1-($C_1$ to $C_4$ alkylaminocarbonyloxy)ethyl groups such as the 1-(methylaminocarbonyloxy)ethyl group.

The quinazolinone library of Formula I can be prepared, using either solution or solid-phase techniques, by combining and reacting an anthranilic acid and an amine component according to the general Reaction Scheme I:

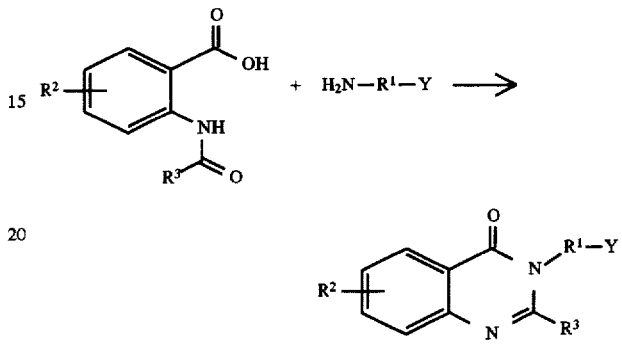

The substituents $R^1$, $R^2$, $R^3$, and Y in Reaction Scheme I have the same meanings as those described above.

As in the above Reaction Scheme I, the amino nitrogen of anthranilic acid can be, though need not be, acylated. Alternatively, the amine component, $H_2N-R^1-Y$, can be acylated as discussed in more detail below. As yet a further alternative, anthranilic acid which is not acylated can be coupled to the amine component, other than aminophenyl carboxylic acids, which coupling is followed by acylation and condensation to get ring closure. This procedure and making styryl derivatives of the resulting quinazolinones is further described in Example III.

Where as depicted in Reaction Scheme I the anthranilic acid is acylated, the anthranilic acid is acylated with any of the above defined $R^3$ groups. Examples of acetylated anthranilic acids, include, but are not limited to, N-(acetyl) anthranilic acid, 3,5-dichloro-N-(acetyl)-anthranilic acid, 3,5-dibromo-N-(acetyl)anthranilic acid, 4,5-difluoro-N-(acetyl)-anthranilic acid, 3,5-dimethyl-N-(acetyl)anthranilic acid, 4-nitro-N-(acetyl)anthranilic acid, and 5-hydroxy-N-(acetyl)anthranilic acid, 3-methoxy anthranilic acid and 3-ethoxyanthranilic acid. The anthranilic acid is preferably acylated and, more preferably, acetylated ($R^3$ is methyl). Preferred acetylated anthranilic acids are N-(acetyl) anthranilic acid, 3,5-dichloro-N-(acetyl)-anthranilic acid, 3,5-dibromo-N-(acetyl)anthranilic acid, 4,5-difluoro-N-(acetyl)-anthranilic acid, 3,5-dimethyl-N-(acetyl)anthranilic acid, and 5-hydroxy-N-(acetyl)anthranilic acid.

When following the procedure detailed in Example III, wherein the anthranilic need not be acetylated, any commercially available anthranilic acid can be used as well as those which can be readily prepared. Preferred examples of such anthranilic acids include, but are not limited to, anthranilic acid, 3, 5-dimethylanthranilic acid, 4, 5-difluoroanthranilic acid, 3-amino-2-naphthoic acid, 3-hydroxyanthranilic acid, 2-amino-3-methoxybenzoic acid, 2-amino-3,4,5,6-tetrafluorobenzoic acid, 2-amino-3-methylbenzoic acid, 2-amino-4-chlorobenzoic acid, 2-amino-4-fluorobenzoic acid, 2-amino-5-bromobenzoic acid, 2-amino-5-chlorobenzoic acid, 2-amino-5-fluorobenzoic acid, 2-amino-5-Iodobenzoic acid, and 2-amino-5-methylbenzoic acid.

Solid-phase techniques may be employed to condense anthranilic acid and the amine component, H$_2$N—R$^1$—Y, of Reaction Scheme I whereby the anthranilic acid is resin bound. For instance, the carboxylic acid functionality of an acylated anthranilic acid can be coupled to resin bound amines and subsequently condensed at 130° C. with the amine component in xylene. Various amino resins are discussed in greater detail below. Alternatively, linkage of the compound to the solid support can be through the anthranilic acid component using aminoterephthalic acid and the like under condensing conditions similar to those discussed in further detail below.

Where anthranilic acid derivatives are used in the preparation of quinazolinones as described above, the starting material, and hence the resulting quinazolinone, is based on a benzene ring. However, quinazolinones can, alternatively, be based on other ring systems, and in particular on heterocyclic rings having the structure of Formula VI:

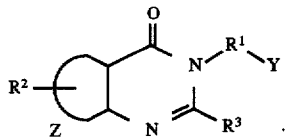

In the above Formula VI, R$^1$, R$^2$, R$^3$, and Y are as defined above and Z is a heteroaromatic ring having from two to six carbons and one or two heteroatoms selected from the group consisting of nitrogen, sulfur and oxygen. Examples of Z ring systems include pyridino, pyrimidino, pyrazino, and pyridazino.

Preferred alternative starting materials to anthranilic acid which provide different ring systems than phenyl include pyridine, such as 2-aminonicotinic acid, and pyrazine, such as 3-aminopyrazine-2-carboxylic acid.

The additional starting material of Reaction Scheme I, the amine component H$_2$N—R$^1$—Y, can be a variety of amines, including aniline derivatives, aliphatic amines, and amino carboxylic acids such as amino acids and aminophenyl carboxylic acids, each of which will be discussed in turn below.

Aniline compounds which can be used as the amine component include, for example, o-toluidine, 4-chloro-2-methylaniline and 2-chloroaniline, and others well known in the art which are readily available or which can easily be synthesized. Where the quinazolinone library is made by combining and reacting anthranilic acid and an aniline, a solution phase reaction generally involves pyrolytically condensing the reactants at approximately 180°–190° C. for about 15 minutes under inert atmosphere either as a melt or in any variety of polar aprotic solvents, such as sulfolane, dimethylformamide (DMF), or 1-methyl-2-pyrolidinone (NMP). Example I below provides further illustration. Where the reaction is carried out in solution phase, generally equimolar amounts or other defined amounts of reactants are use. Again, the reaction can done by solid-phase techniques as described above and in such instances excess reactants are used. In addition, condensation using various drying agents, such as phosphorus trichloride (PCl$_3$), phosphorus oxychloride (POCl$_3$), or phosphorus pentoxide (P$_2$O$_5$), in toluene can be done at lower temperatures.

In instances where the anthranilic acid is not acylated as described above, aniline can alternatively be acylated. For example, Acetanilide or N-(acetyl)-toluidine can be used. The same reaction conditions as with non-acylated aniline apply, except that the reaction generally takes up to two hours.

Alternatively, as described above, the amine component, H$_2$N—R$^1$—Y, of Reaction Scheme I can be an aliphatic amine. Aliphatic amines can be condensed with anthranilic acid under generally the same conditions as used when condensing the aniline compounds.

The amine component of Reaction Scheme I can also be an amino carboxylic acid, including amino acids and aminophenyl carboxylic acids. The amino acid can be any one of the twenty naturally-occurring amino acids or the D-form of any one of the naturally-occurring amino acids. In addition, the invention includes the use of non-naturally occurring amino acids, such as norleucine ("Nle"), norvaline ("Nva"), β-Ala, L- or D-naphthalanine, ornithine ("Orn"), homoarginine (homoArg) and others well known in the peptide art, such as those described in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, both of which are incorporated herein by reference. Amino acids and amino acid analogs can be purchased commercially (Sigma Chemical Co.; Advanced Chemtec) or synthesized using methods known in the art.

The amino acids are indicated herein by either their full name or by the commonly known three letter code. Further, in the naming of amino acids, "D-" designates an amino acid having the "D" configuration, as opposed to the naturally occurring L-amino acids. Where no specific configuration is indicated, one skilled in the art would understand the amino acid to be an L-amino acid. The amino acids can, however, also be in racemic mixtures of the D- and L-configuration.

As used herein, the phrase "any one of the twenty naturally-occurring amino acids" means any one of the following: Ala, Arg, Asn, Asp, Cys, Gln, Glu, Gly, His, Ile, Leu, Lys, Met, Phe, Pro, Ser, Thr, Trp, Tyr, and Val. As used herein, the language "the D-form of a naturally-occurring amino acid" means the D-isomer of any one of these naturally-occurring amino acids, with the exception of Gly, which does not occur as D or L isomers.

Preferred amino acids are L- and D-Ala, L- and D-Phe, substituted L- and D-Phe, such as for example p-chlorophe, p-fluorophe, and p-iodophe, Gly, L- and D-Ile, L- and D-Leu, L- and D-Lys, L- and D-Arg, L- and D-Glu, L- and D-Ser, L- and D-Thr, L- and D-Val, L- and D-Tyr, substituted L- and D-Tyr, such as O-ethylTyr, L-Nle, L-Nva, L- and D-Trp, β-Ala, cyclohexylalanine, β-thienylalanine, L- and D-naphthylalanine. When these preferred amino acids are used, R$^1$ is preferably the α-carbon and the side chain of these respective amino acid as provided above in Tables I and II.

Alternative preferred aminocarboxylic acids beside the above described amino acids include 7-aminoheptanoic acid, L-α-aminobutyric acid, γ-aminobutyric acid, ε-aminocaproic acid, and aminophenyl carboxylic acids, such as 4-aminobenzoic acid, 4-aminophenylacetic acid, 4-aminophenylbutyric acid, 3-aminophenylacetic acid, 3-amino-2-methylbenzoic acid, 4-amino-2-chlorobenzoic acid, 4-aminosalicylic acid.

When aminocarboxylic acids are used as the amine component, the method of synthesizing the quinazolinones is most usually and practically conducted using a solid-support. However, there is no reason the synthesis cannot be done in solution phase. Resins which can serve as solid supports are well known in the art and include amino resins and hydroxy resins which are polymers crosslinked with amino and hydroxy groups, respectively. Such resins include 4-methylbenzhydrylamine (MBHA), 4-methylbenzhydrylamine-copoly(styrene-1% divinylbenzene), 4-(oxymethyl)-phenylacetamido methyl (Pam), 4-(oxymethyl)-phenylacetamido methyl-copoly(styrene-1% divinylbenzene), 4-(hydroxymethyl)phenoxymethyl-copoly(styrene-1% divinylbenzene) (Wang resin), all of which are commercially available, or to p-nitrobenzophenone oxime polymer (oxime resin), which can be synthesized as described by De Grado and Kaiser, J. Org. Chem., 47:3258 (1982), which is incorporated herein by reference. Recently, a polyethylene-grafted cross-linked polystyrene resin termed TentaGel has been made commercially available by RappPolymere (Tubingen, Germany), which resin can also be used with the present invention. These and other types of resins well known in the art can be used in the subject invention.

The amino carboxylic acid can be attached to the resin by coupling procedures well known in the art and as described in the ensuing Examples. During such attachment to the resin, at least the α-amino group of an amino acid, as well as the α-amino of other amino carboxylic acids, is protected with an amino-protecting group. However, with the relatively non-nucleophilic anilino group of an aminophenyl carboxylic acid, protection is not required. Where necessary, side chain functional groups of amino acids are also protected as is commonly done in the field. Prior to condensation of the amino carboxylic acid with anthranilic acid, at least the α-amino protecting group is removed with, for example, trifluoroacetic acid (TFA) for the removal of the Boc group and piperidine for the removal of the Fmoc group. The condensation reaction can be done under the same conditions as those described above and as provided in Example II.

Once the initial quinazolinone structure of Formula I is prepared by any one of the above described methods the quinazolinone mixture can be further chemically transformed to extend the range and chemical diversity of the compounds. Using the "libraries from libraries" concept, as described in Ostresh et al., Proc. Natl. Acad. Sci., 91:11138–11142 (1994), various libraries of quinazolinone derivatives can be prepared by chemically altering the initial quinazolinone library.

One such chemical transformation is to convert the quinazolinone library to a library of five or more styryl derivatives of quinazolinone having the Formula II:

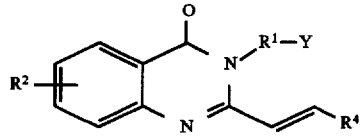

Styryl derivatives can be prepared by treating the quinazolinone product with a non-nucleophilic base under anhydrous condition with lithium t-butoxide in tetrahydrofuran (LiOtBu/THF) for approximately 15 min., followed by adding a non-enolizable aldehyde. The aldehyde can be any one which results in $R^4$ as described above. Exemplary aldehydes include 2,4-dichlorobenzaldehyde, 4-hydroxybenzaldehyde, 2-naphthaldehyde, 2,5-dimethylbenzaldehyde, 3,4-difluorobenzaldehyde, 4-bromobenzaldehyde, 3-(4-methylphenoxy)benzaldehyde, para-(anisaldehyde), 3-ethoxy-4-hydroxybenzaldehyde, 4-biphenylcarboxaldehyde, 4-nitrobenzaldehyde, benzaldehyde, 10-chloro-9-anthraldehyde, 6-methyl-2-pyridinecarboxaldehyde, 2-methoxy-1-naphthaldehyde, 2,4,5-trimethoxybenzaldehyde, 4-(dimethylamino)benzaldehyde, and 2-butylacrolein. Preferred aldehydes are 2,4-dichlorobenzaldehyde, 2-naphthaldehyde, 2,5-dimethylbenzaldehyde, 3,4-difluorobenzaldehyde, 4-bromobenzaldehyde, 3-(4-methylphenoxy)benzaldehyde, para-(anisaldehyde), 4-biphenylcarboxaldehyde, benzaldehyde, 6-methyl-2-pyridinecarboxaldehyde, 2-methoxy-1-naphthaldehyde, 2,4,5-trimethoxybenzaldehyde, and 4-(dimethylamino)benzaldehyde as well as others provided in Examples II and III.

The library of styrene derivatives itself can be further chemically altered. For example, the styrene derivatives can be epoxidized with peroxoacids, such as m-chloroperbenzoic acid. Alternatively, or in addition thereto, the carbonyl can be reduced by standard procedures, for example, by reduction with lithium aluminum hydride (LiAlH$_4$) in THF. Similarly, the styrene compounds can be N-alkylated as described below.

In another embodiment of the present invention, the quinazolinone library can be reduced with, for example, a borohydride reagent under the usual conditions, to prepare a library five or more quinazolinone derivatives of Formula III:

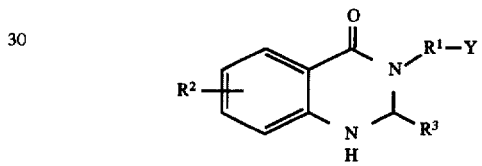

Alternatively, or in additional thereto, in yet another embodiment of the invention, the basic amine of the quinazolinones can be alkylated to prepare a library of compounds of Formula IV:

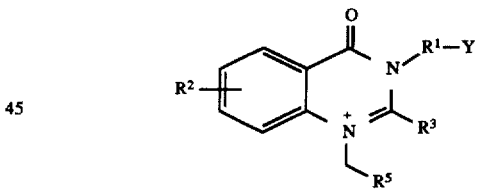

To prepare these or related N-alkylated derivatives, the amine is first reduced with a borohydride reagent, followed by alkylation with alkylating agents of the $R^5$ groups described above. Such alkylating agents include $R^5$ groups derivatized with a bromo, iodo, triflate or methylsulfonate groups. Other alkylating derivatives of the $R^5$ group are well known. Finally, the compounds are reoxidized to obtain the quaternary amine using dichlorodicyanoquinone (DDQ).

An alternative approach to obtain libraries of much larger diversity, without having to form styrene 5derivatives as described above, is to use N-(2-bromoacetyl)anthranilic acid and two amine components, such as two anilines, as provided in Reaction Scheme II:

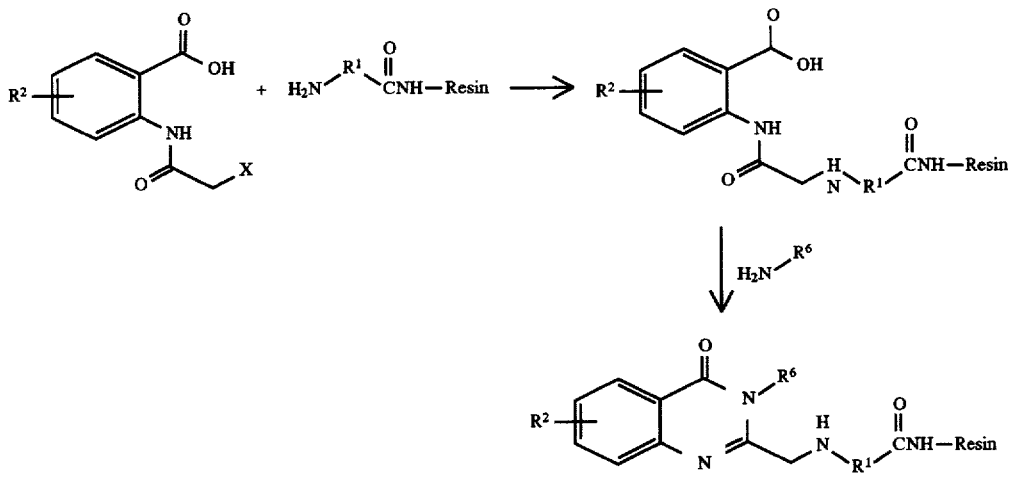

In Reaction Scheme II, $R^1$, $R^2$, and $R^6$ are as defined above. The substituent X is a leaving group, such as bromo, iodo, triflate, methylsulfonate, or phenylsulfonate. The first amine component can be condensed with, for example, N-(bromoacetyl)anthranilic acid in sulfolane at 35° C. for one hour. N-(bromoacetyl)anthranilic can be prepared by acylating anthranilic acid with bromoacetyl chloride. Generally, to ensure that a tertiary amine does not result the first amine component is protected with an amino-protecting group, such as Didyl. The second amine component, such as a second aniline, can be condensed in sulfolane at approximately 200° C. for about two hours.

Approaches for preparing the libraries of quinazolinones or quinazolinone derivatives are several and can be any of those well known in the art. For example, preparation of the libraries can be by the "split synthesis" method, as described in Gallop et al., J. Med. Chem., 37:1233–1251 (1994). The split synthesis procedure involves dividing a resin support into n equal fractions, in a separate reaction carry out a single reaction to each aliquot, and then thoroughly mixing all the resin particles together. Repeating the protocol for a total of x cycles can produce a stochastic collection of up to $n^x$ different compounds. For instance, in Example II the split synthesis approach was used to prepare a mixture of thirty five aminocarboxylic acids. An alternative format is, preparing sublibraries in the $O_3O_2X_1$ format, wherein two positions on the compounds, $O_3$ and $O_2$, are explicitly defined and a third position, $X_1$, varies. Such sublibraries can be conveniently prepared by the tea-bag technique, as is known in the art, and described, for example in U.S. Pat. No. 4,631,211 to Houghten and Houghten et al., Proc. Natl. Acad. Sci., 82:5131–5135 (1985), as well as described in Example II. Alternatively, or in addition thereto, the iterative selection and enhancement process of screening and sublibrary resynthesis can be employed. For example, a sublibrary of various $R^1$ substituents can be screened to select the most active $R^1$ substituent. The quinazolinone having the most active $R^1$ is then resynthesized and with the $R^1$ position being defined, a new $R^2$ position mixture library is prepared, screened, and the most active $R^2$ selected. The above process can then be repeated to identify $R^3$ and the other most active R substituents on the quinazolinone ring. In yet another approach, the positional scanning technique, only a single position is defined in a given sublibrary and the most preferred substituent at each position of the compound is identified.

The advantage of synthetic combinatorial libraries (SCLs) made up of mixtures of tens of millions of different compounds is that they can be used to rapidly identify individual, active compounds without the need to individually synthesize, purify, and test every single compound. Since the libraries are in solution (i.e., not attached to a bead, pin, phage, glass, etc.) they can be screened in virtually any assay system. Here, the libraries can be screened in a variety of described, for example, in Parmar and Seth, Canadian J. Of Biochem., 43:1179–1185 (1965), Joshi et al., Ind. J. Exp. Biol., 15:1064–1066 (1977), Leszkovszky et al., Aeta Physioloaica, 6:81–90, Gujral et al., Ind. J. Med. Res., 45:207–211 (1957), all of which are incorporated herein by reference.

The following Examples are intended to illustrate but not limit the present invention.

EXAMPLE I

Solution-Phase Preparation of a Qouinazolinone Library

This Example provides a solution-phase combinatorial synthesis of a quinazolinone library.

Following the below Reaction Scheme III, in solution phase, N-acetyl anthranilic acids were condensed with aniline compounds to prepare a library of quinazolinones.

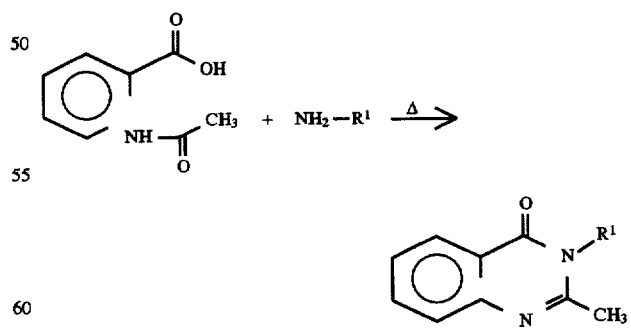

Specifically, in a single 10 ml test tube, 1.5 equimolar (Eq) each of two different N-(acetyl) anthranilic acids, N-(acetyl)anthranilic acid (1336 mg; 1.5 Eq) and 3,5-dichloro-N-(acetyl)anthranilic acid (1860; 1.5 Eq) (identified below as 1 and 2, respectively), were combined and pyrolytically condensed for 15 min. at 180°–190° C. with one equimolar amount each of three aniline compounds, o-toluidine (536 μl; 1 Eq), 4-chloro-2-methylaniline (597 μl; 1 Eq) and 2-chloroaniline (525 μl; 1 Eq) (identified below as 3, 4 and 5, respectively).

(1)
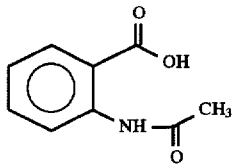

(2)
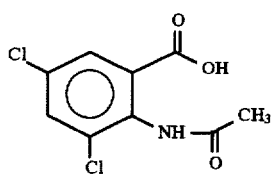

EXAMPLE II

Solid-Phase Preparation of 3,000 Styryl Derivatives of Quinazolinone

This Example provides a solid-phase combinatorial synthesis of a library containing approximately 3000 styryl derivatives of quinazolinones. This library was prepared from acetylated anthranilic acid as a starting material.

1. This Example follows the general Reaction Scheme IV as follow:

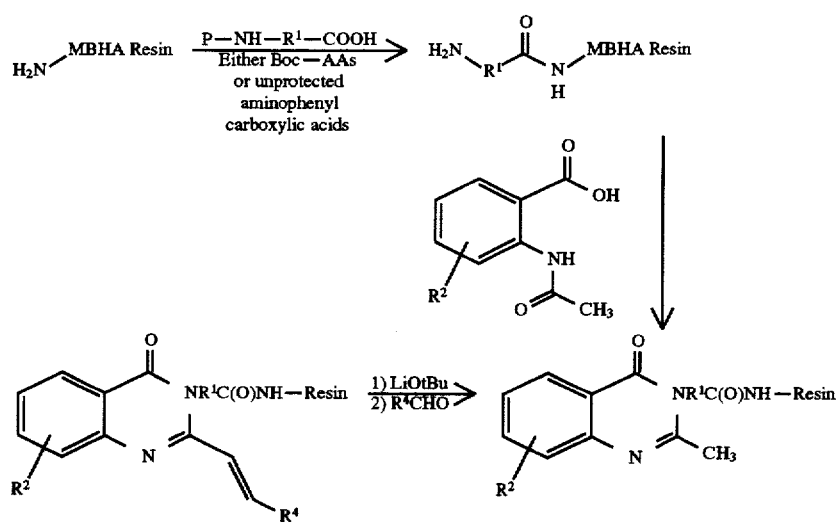

-continued (3)
(4)
(5)
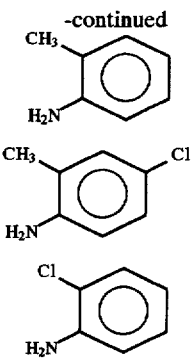

RP-HPLC purification (Beckman System Gold, Los Angeles, Calif.; reverse-phase, acetonitrile/TFA system) and Matrix Assisted Laser Desorption Ionization-Mass Spectomerty (MALDI-MS) (Cratos, Columbia, Md.) showed the presence of the six expected quinazolinone products as well as starting material.

In Reaction Scheme IV, $R^1$, $R^2$, $R^3$, and $R^4$ are the respective R groups based on the starting materials provided in Table III below. The P group is an amino-protecting group as defined above.

As shown by Reaction Scheme IV, preparation of the library containing styryl derivatives of quinazolinones involved the following steps. Briefly, first, thirty five diverse amino carboxylic acids, varying at $R^1$ and including various Boc-protected amino acids (Boc-AAs) and differing aminophenyl carboxylic acids, were coupled to MBHA resin. The resins were then mixed, followed by condensation of seven acetylated anthranilic acids, each differing by their $R^2$ substituent, to the mixtures of resin bound amino carboxylic acids. Third, the resulting quinazolinone product was treated with LiOtBu/THF and thirteen different benzaldehydes having differing $R^4$ groups were added to arrive at a library of approximately 3000 styryl derivatives of quinazolinone. Finally, the compounds were cleaved from the MBHA resin and tested for biological activity.

The library was prepared in the $O_3O_2X_1$ format in which there were 91 mixtures of 35 compounds. The starting materials used are listed in Table III.

washed with MeOH, and dried under vacuum. Based upon synthesis and cleavage, for each of the thirty five aminocarboxylic acids reaction completion was <95%.

TABLE III

| #  | ALDEHYDE | ANTHRANILIC ACID DERIVATIVE | AMINO CARBOXYLIC ACID |
|----|----------|-----------------------------|------------------------|
| 1  | 2,4-DICHLOROBENZALDEHYDE | ANTHRANILIC ACID | BOC-L-ALANINE |
| 2  |          |                  | BOC-L-PHENYLALANINE |
| 3  | 2-NAPHTHALDEHYDE | 3,5-DICHLOROANTHRANILIC ACID | BOC-GLYCINE |
| 4  | 2,5-DIMETHYLBENZALDEHYDE | 3,5-DIBROMOANTHRANILIC ACID | BOC-L-ISOLEUCINE |
| 5  | 3,4-DIFLUOROBENZALDEHYDE | 3,5-DIMETHYLANTHRANILIC ACID | BOC-L-LEUCINE |
| 6  | 4-BROMOBENZALDEHYDE | 4,5-DIFLUOROANTHRANILIC ACID | BOC-L-ARGININE |
| 7  | 3-(4-METHYLPHENOXY)BENZALDEHYDE | 5-HYDROXYANTHRANILIC ACID | BOC-L-SERINE |
| 8  | PARA-ANISALDEHYDE | 3-AMINO-2-NAPHTHOIC ACID | BOC-L-THREONINE |
| 9  |          |                  | BOC-L-VALINE |
| 10 | 4-BIPHENYLCARBOXALDEHYDE |     | BOC-L-TYROSINE |
| 11 |          |                  | BOC-D-ALANINE |
| 12 | BENZALDEHYDE |              | BOC-D-PHENYLALANINE |
| 13 |          |                  | BOC-D-ISOLEUCINE |
| 14 | 6-METHYL-2-PYRIDINECARBOXALDEHYDE | | BOC-D-LEUCINE |
| 15 | 2-METHOXY-1-NAPHTHALDEHYDE |  | BOC-D-ARGININE |
| 16 | 2,4,5-TRIMETHOXY BENZALDEHYDE | | BOC-D-SERINE |
| 17 | 4-(DIMETHYLAMINO)BENZALDEHYDE | | BOC-D-THREONINE |
| 18 |          |                  | BOC-D-VALINE |
| 19 |          |                  | BOC-D-TYROSINE |
| 20 |          |                  | BOC-L-NORLEUCINE |
| 21 |          |                  | BOC-L-NORVALINE |
| 22 |          |                  | BOC-β-ALANINE |
| 23 |          |                  | BOC-L-α-AMINOBUTYRIC ACID |
| 24 |          |                  | BOC-γ-AMINOBUTYRIC ACID |
| 25 |          |                  | BOC-ε-AMINOCAPROIC ACID |
| 26 |          |                  | BOC-L-NAPHTHYLALANINE |
| 27 |          |                  | BOC-D-NAPHTHYLALANINE |
| 28 |          |                  | BOC-7-AMINOHEPTANOIC ACID |
| 29 |          |                  | 4-AMINOBENZOIC ACID |
| 30 |          |                  | 4-AMINOPHENYLACETIC ACID |
| 31 |          |                  | 4-AMINOPHENYLBUTYRIC ACID |
| 32 |          |                  | 3-AMINOPHENYLACETIC ACID |
| 33 |          |                  | 3-AMINO-2-METHYLBENZOIC ACID |
| 34 |          |                  | 4-AMINO-2-CHLOROBENZOIC ACID |
| 35 |          |                  | 4-AMINOSALICYLIC ACID |

1. Coupling of Amino Carboxylic Acids to MBHA Resin

The thirty five diverse amino carboxylic acid provided in Table III, varying at $R^1$ and including various Boc-AAs and differing aminophenyl carboxylic acids, were coupled to MBHA resin as follows.

Thirty five polypropylene mesh packets (tea-bags, ~2" square, 65μ; McMaster Carr, Chicago, Ill.) of (0.6 g, 0.93 meq/g) MBHA resin were prepared, washed with dichloromethane (DCM) (2×, ~ 5 ml each), neutralized with 5% diisopropylethylamine/DCM (3×, ~ 5 ml each), and washed with DCM (2×, ~ 5 ml each). Each resin packet was individually coupled overnight (~ 16 hr, except for Gly, 1 hr.) by adding 10× amino acid in DCM (0.2M) or aminophenylcarboxylic acid in dimethylformamide (DMF) followed by diisopropylcarbodiimide/DCM (10×, 0.2M) for a final concentration of 0.1M. 5% DMF was used to solubilize the Arg and Ser derivatives. N-hydroxybenzotriazole (HOBt; 10×) was added to the aminophenyl carboxylic acids couplings. The relatively non-nucleophilic anilino groups of the aminophenylcarboxylic acids were unprotected. Following coupling completion, resin packets were washed with DCM (1×), isopropanol (IPA) (2×), and DCM (2×). The amino acid was deprotected with 55% TFA in DCM. Each packet was then opened and the resin carefully washed into a common vessel using alternating DCM and MeOH washes (final volume, ~ 200 ml). The resin was mixed using a magnetic stir bar for 2.5 hr. The resin was then filtered.

2. Quinazolinone Library by Condensation of Acetylated Anthranilic Acids to the Mixture of Resin Bound Amino Carboxylic Acids Seven acetylated anthranilic acids, each differing by their $R^2$ substituent and listed in Table III, were condensed to the above prepared mixture of resin bound Boc-AAs and aminophenylcarboxylic acids.

a. Acetylation of the Anthranilic Acids

Each anthranilic acid listed in Table III was first acetylated. Five to ten grams of each acetylated anthranilic acid was prepared by adding 1.5× neat acetic anhydride ($Ac_2O$) to 0.2M anthranilic acid/THF and allowing the reaction to proceed at room temperature for 1 hr. Following addition of an equal volume of IPA, the solution was evaporated to dryness on a rotary evaporator, redissolved and evaporated from IPA, followed by THF. Reaction completion was confirmed by RP-HPLC and MALDI-MS.

b. Condensation Reaction

Each acetylated anthranilic acid (5×) in sulfolane (~0.4M, tetramethylene sulfone, 35° C., 10 ml each) was added to the amino acid/aminophenyl carboxylic acid resin mixtures (1 g) in individual 50 ml Kimax tubes and heated at 190° C. for 2 hr. Each resin was then washed by filtration with DMF (2×), MeOH (1×), DMF (2×), MeOH (1×), DMF (2×), MeOH (1×), DMF (2×). Resins were then washed with MeOH and dried under high vacuum.

Individual controls included the following. As representative of the amino acids, resin-bound phenylalanine was condensed with each anthranilic acid, the products were cleaved and analyzed by HPLC and MS. As representative of the aminophenylcarboxylic acids, each of the resin-bound aminophenylcarboxylic acids was condensed with N-(acetyl)anthranilic acid. Products were removed from resin and analyzed. Using the same instruments and conditions as above, RP-HPLC and MALDI-MS of individual control compounds indicated that compounds of 60–95% purity were formed and in all cases the expected product was the major component.

3. Styryl Derivatives of the Quinazolinones

From the above made library of quinazolinones a library of styryl derivatives of quinazolinone were prepared as follows.

a. Preparation of Aldehyde

Stock solutions of each aldehyde listed in Table III were prepared based upon the use of seven 50 mg packets of resin for each benzaldehyde. 100× over resin substitution was added to 25 ml THF in 50 ml Kimax tubes. Anhydrous MgSO$_4$ (2–5 g) was added to each tube, followed by capping. Following centrifugation, ½ of the solution was removed (in a glovebox under nitrogen atmosphere) for use in the reaction.

b. Styryl Derivatization

Ninety-one mesh packets (13 packets—one per benzaldehyde—for each of the seven OX resins) containing 50 mg resin were prepared. To each set of 7 packets in 50 ml KIMAX tubes, LiOtBu in THF (10×, 0.2M) was added under anhydrous conditions and allowed to react for 15 min. Following washes with anhydrous THF (2×), aldehyde stock solution (12.5 ml, 50× over resin substitution) and LiOtBu (10×, 1M) were added. The tubes were capped and placed in a 70° C. oil bath overnight (~16 hr.). The resin packets were then washed with DMF (1×), DCM (2×), followed by 5 alternating washes of DMF and MeOH. The packets were dried under high vacuum, followed by treatment with hydrogen fluoride (5% anisole, 1 hr., 0° C.) to cleave compounds from the MBHA resin.

As a control for the aldehyde condensation, the following was done. For each aldehyde two quinazolinone resins were added to each reaction vessel to monitor the condensation. The two quinazolinone resins were the result of (1) resin-bound aminophenyl acetic acid condensed with N-(acetyl)anthranilic acid and (2) resin-bound phenylalanine condensed with N-(acetyl)anthranilic acid. Resins were cleaved and products analyzed by HPLC and MS. In addition, a post library control was done. This control confirmed that the procedure used to add the aldehyde, and in particular the addition of base, did not affect the aminocarboxylic acids used in the library. Resins were made of each of the thirty five and aminocarboxylic acids used in the library. The resins were then condensed, first, with N-(Acetyl)anthranilic acid and then with 6-Methyl-2-pyridine carboxaldehyde. Upon cleavage from resin, products were analyzed by HPLC and MS.

Percent yields based upon starting resin substitution are listed in Table IV. Reference numbers ("REF. #") in Table IV first reference the aldehyde number provided in starting materials Table III, followed by the anthranilic acid derivative number also provided in Table III. For example, "1—1" hereinbelow in Table IV means the yields for the reactants 2,4-Dichlorobenz-aldehyde, N-(acetyl)anthranilic acid and each of the thirty five amino carboxylic acids of Table III. Similarly, reference number "6–3" means 4-Bromobenzaldehyde, 3,5-Dichloroanthranilic acid and the thirty five amino carboxylic acids.

TABLE IV

| REF. # | EXP. YD. | THEO. YD. | % YD. | REF. # | EXP. YD. | THEO. YD. | % YD. |
|---|---|---|---|---|---|---|---|
| 1-1 | 8.7 | 15.7 | 55.4 | 10-5 | 9.2 | 16.7 | 55.1 |
| 3-1 | 10.6 | 15.1 | 70.2 | 12-5 | 7.8 | 14.0 | 55.7 |
| 4-1 | 10.1 | 14.3 | 70.6 | 14-5 | 13.3 | 14.5 | 91.7 |
| 5-1 | 10.2 | 14.6 | 69.9 | 15-5 | 11.6 | 16.8 | 69.0 |
| 6-1 | 13.7 | 16.1 | 85.1 | 16-5 | 13.0 | 17.2 | 75.6 |
| 7-1 | 11.6 | 17.1 | 67.8 | 17-5 | 12.3 | 15.5 | 79.4 |
| 8-1 | 11.9 | 14.3 | 83.2 | 1-6 | 7.2 | 16.6 | 43.4 |
| 10-1 | 11.1 | 16.0 | 69.4 | 3-6 | 7.5 | 15.9 | 47.2 |
| 12-1 | 9.8 | 13.3 | 73.7 | 4-6 | 9.2 | 15.2 | 60.5 |
| 14-1 | 13.2 | 13.8 | 95.7 | 5-6 | 10.0 | 15.4 | 64.9 |
| 15-1 | 12.3 | 16.1 | 76.4 | 6-6 | 9.7 | 16.9 | 57.4 |
| 16-1 | 12.6 | 16.5 | 76.4 | 7-6 | 8.4 | 17.9 | 46.9 |
| 17-1 | 9.6 | 14.8 | 64.9 | 8-6 | 12.4 | 15.2 | 81.6 |
| 1-3 | 5.8 | 17.4 | 33.3 | 10-6 | 12.2 | 16.8 | 72.6 |
| 3-3 | 6.7 | 16.7 | 40.1 | 12-6 | 10.5 | 14.2 | 73.9 |
| 4-3 | 6.3 | 16.0 | 39.4 | 14-6 | 14.7 | 14.7 | 100.0 |
| 5-3 | 6.4 | 16.2 | 39.5 | 15-6 | 10.8 | 17.0 | 63.5 |
| 6-3 | 5.0 | 17.7 | 28.2 | 16-6 | 11.8 | 17.3 | 68.2 |
| 7-3 | 6.9 | 18.6 | 37.1 | 17-6 | 12.5 | 15.7 | 79.6 |
| 8-3 | 6.7 | 16.0 | 41.9 | 1-7 | 13.5 | 16.1 | 83.9 |
| 10-3 | 6.5 | 17.6 | 36.9 | 3-7 | 12.2 | 15.5 | 78.7 |
| 12-3 | 5.3 | 15.0 | 35.3 | 4-7 | 11.7 | 14.7 | 79.6 |
| 14-3 | 11.3 | 15.5 | 72.9 | 5-7 | 12.8 | 15.9 | 85.3 |
| 15-3 | 7.8 | 17.7 | 44.1 | 6-7 | 11.3 | 16.5 | 68.5 |
| 16-3 | 7.0 | 18.1 | 38.7 | 7-7 | 13.1 | 17.4 | 75.3 |
| 17-3 | 9.2 | 16.5 | 55.8 | 8-7 | 13.4 | 14.7 | 91.2 |
| 1-4 | 5.4 | 19.2 | 28.1 | 10-7 | 10.1 | 16.4 | 61.6 |
| 3-4 | 4.8 | 18.6 | 25.8 | 12-7 | 9.9 | 13.7 | 72.3 |
| 4-4 | 4.8 | 17.9 | 26.8 | 14-7 | 11.3 | 14.2 | 79.6 |
| 5-4 | 5.2 | 18.2 | 28.6 | 15-7 | 12.6 | 16.5 | 76.4 |
| 6-4 | 4.9 | 19.5 | 25.1 | 16-7 | 11.2 | 16.9 | 66.3 |
| 7-4 | 6.3 | 20.4 | 30.9 | 17-7 | 12.8 | 15.2 | 84.2 |
| 8-4 | 6.4 | 18.0 | 35.6 | 1-8 | 9.0 | 16.9 | 53.3 |
| 10-4 | 4.0 | 19.5 | 20.5 | 3-8 | 10.6 | 16.3 | 65.0 |
| 12-4 | 5.5 | 17.0 | 32.4 | 4-8 | 14.4 | 15.5 | 92.9 |
| 14-4 | 10.4 | 17.5 | 59.4 | 5-8 | 11.4 | 15.8 | 72.2 |
| 15-4 | 7.5 | 19.6 | 38.3 | 6-8 | 7.7 | 17.3 | 44.5 |
| 16-4 | 7.7 | 19.9 | 38.7 | 7-8 | 7.6 | 18.2 | 41.8 |
| 17-4 | 10.2 | 18.4 | 55.4 | 8-8 | 9.4 | 15.6 | 60.3 |
| 1-5 | 8.6 | 16.4 | 52.4 | 10-8 | 8.9 | 17.2 | 51.7 |
| 3-5 | 8.6 | 15.7 | 54.8 | 12-8 | 9.5 | 14.5 | 65.5 |
| 4-5 | 8.2 | 15.0 | 54.7 | 14-8 | 12.6 | 15.1 | 83.4 |
| 5-5 | 11.0 | 15.3 | 71.9 | 15-8 | 12.7 | 17.3 | 73.4 |
| 6-5 | 10.5 | 16.8 | 62.5 | 16-8 | 13.6 | 17.7 | 76.8 |
| 7-5 | 11.1 | 17.7 | 62.7 | 17-8 | 11.1 | 16.0 | 69.4 |
| 8-5 | 10.6 | 15.0 | 70.7 | | | | |

As can be seen from Table IV, approximately 3,000 styryl derivatives of quinazolinone, a library from a library, were successfully prepared with reasonable yields.

EXAMPLE III

Solid-Phase Preparation of 35,700 Styryl Derivatives of Quinazolinine

This Example provides a solid-phase combinatorial synthesis of a library containing approximately 35,700 styryl derivatives of quinazolinone. Unlike Example II, this library was prepared using anthranilic acid starting material which acids were not previously acetylated.

This Example follows the general Reaction Scheme V as follows:

27

Step 1
[Amino acid incorporation-R₁]

a) Protected amino acid coupling
b) Deprotection

Step 2
[Anthranilic acid incorporation-R₂]

a) Anthranilic acid coupling b) Acetylation c) Condensation

Step 3
[Benzaldehyde incorporation-R₄]

a) Styrene formation

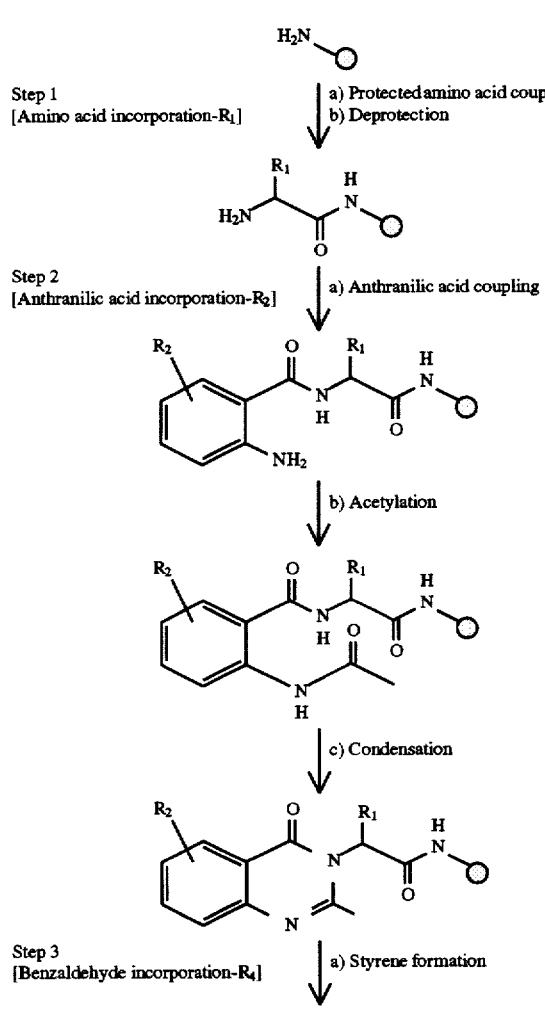

28

-continued

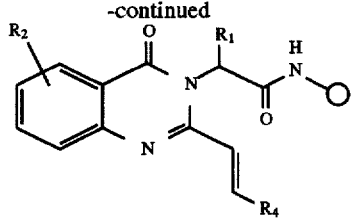

In Reaction Scheme V, $R^1$, $R^2$, $R^3$, and $R^4$ are the respective R groups based on the starting materials provided in Table V below.

As shown by Reaction Scheme V, preparation of the library containing 35,700 styryl derivatives of quinazolinone involved the following steps. Briefly, thirty five diverse Boc-protected amino acids varying at $R^1$ were coupled to MBHA resin. After deprotection of the amino acids, the resins were then mixed and fifteen anthranilic acids, each differing by their $R^2$ substituent, were condensed with the resin bound amino acids. Following anthranilic acid coupling, the compounds were acetylated and condensation was subsequently carried out to close the ring and form the respective quinazolinones. The corresponding styryl derivatives were formed by treating the resulting quinazolinone product with LiOtBu/THF and 68 different aldehydes to arrive at a library of approximately 35,700 styryl compounds.

The library was prepared in the OXX format in which $R^4$ position was a defined position, while $R^1$ and $R^2$ were mixtures. The library was synthesized using a simultaneious multiple synthesis technique, the tea-bag technique, as previously described, in which aliquots of resin are contained within polypropylene mesh to allow common procedures to be performed simultaneously. Mixture positions were obtained using the split synthesis method, as described above. The starting materials used are listed in Table V.

TABLE V

| #  | ALDEHYDE | ANTHRANILIC ACID DERIVATIVE | AMINO CARBOXYLIC ACID |
|----|----------|------------------------------|------------------------|
| 1  | Benzaldehyde | Anthranilic Acid | Boc-L-Alanine |
| 2  | 2-Bromobenzaldehyde | | Boc-L-Glutamic acid-benzyl ester |
| 3  | | | Boc-L-Phenylalanine |
| 4  | | | Boc-Glycine |
| 5  | 2-Fluorobenzaldehyde | 3,5-Dimethylanthranilic Acid | |
| 6  | | 4,5-Difluoroanthranilic Acid | |
| 7  | 2-Methoxybenzaldehyde | | Boc-L-Lysine(2-Cl—Z) |
| 8  | 3-Bromobenzaldehyde | 3-Amino-2-Naphthoic Acid | Boc-L-Leucine.H₂O |
| 9  | 3-Cyanobenzaldehyde | 3-Hydroxyanthranilic Acid | |
| 10 | 3-Fluorobenzaldehyde | | |
| 12 | 3-Methoxybenzaldehyde | 2-Amino-3-Methoxybenzoic Acid | Boc-L-Serine (O-Benzyl) |
| 13 | 3-Methylbenzaldehyde | | Boc-L-Threonine(O-Benzyl) |
| 15 | 3-(Trifluoromethyl)benzaldehyde | 2-Amino-3,4,5,6-Tetrafluorobenzoic Acid | |
| 16 | | 2-Amino-3-Methylbenzoic Acid | Boc-L-Tyrosine(2-Br—Z) |
| 17 | 4-Bromobenzaldehyde | | Boc-D-Alanine |
| 18 | | 2-Amino-4-Chlorobenzoic Acid | Boc-D-Glutamic acid-benzyl ester |
| 19 | 4-Cyanobenzaldehyde | 2-Amino-4-Fluorobenzoic Acid | Boc-D-Phenylalanine |
| 20 | 4-Fluorobenzaldehyde | 2-Amino-5-Bromobenzoic Acid | |

TABLE V-continued

| # | ALDEHYDE | ANTHRANILIC ACID DERIVATIVE | AMINO CARBOXYLIC ACID |
|---|---|---|---|
| 21 | 4-(Dimethylamino)benzaldehyde | 2-Amino-5-Chlorobenzoic Acid | |
| 22 | 4-Isopropylbenzaldehyde | 2-Amino-5-Fluorobenzoic Acid | Boc-L-Lysine(2-Cl—Z) |
| 23 | 4-Methoxybenzaldehyde | 2-Amino-5-Iodobenzoic Acid | Boc-D-Leucine.$H_2O$ |
| 24 | | 2-Amino-5-Methylbenzoic Acid | |
| 25 | 4-(Methylcarboxylate)benzaldehyde | | |
| 26 | 4-(Methylthio)benzaldehyde | | |
| 27 | 4-Propoxybenzaldehyde | | Boc-D-Serine (O-Benzyl) |
| 28 | 4-(Trifluoromethyl) benzaldehyde | | Boc-D-Threonine (O-Benzyl) |
| 29 | 3,5-Dimethoxybenzaldehyde | | |
| 30 | 2,3-Difluorobenzaldehyde | | |
| 31 | 2,5-Dimethylbenzaldehyde | | Boc-D-Tyrosine (2-Br—Z) |
| 32 | 2,4-Dichlorobenzaldehyde | | Boc-L-Norvaline |
| 33 | | | Boc-L-Norleucine |
| 35 | | | Boc-L-3-(2-Naphthyl)-Alanine |
| 36 | 2-Chloro-6-fluorobenzaldehyde | | Boc-L-Cyclohexylalanine |
| 38 | 3-Bromo-4-fluorobenzaldehyde | | Boc-P-Chloro-L-Phenylalanine |
| 39 | 3,4-Dibenzyloxybenzaldehyde | | Boc-p-Fluoro-L-Phenylalanine |
| 40 | 3,4-Dichlorobenzaldehyde | | |
| 41 | 3,4-Difluorobenzaldehyde | | |
| 42 | 3-Fluoro-4-methoxybenzaldehyde | | Boc-β-Thienyl-L-Alanine |
| 43 | | | Boc-O-Ethyl-L-Tyrosine |
| 45 | 3-Methyl-4-methoxybenzaldehyde | | Boc-L-α-Aminobutyric acid |
| 46 | 2,3,5-Trichlorobenzaldehyde | | |
| 47 | 2,4,5-Trimethoxybenzaldehyde | | |
| 50 | 1,4-Benzodioxan-6-carboxaldehyde | | |
| 51 | 3,4-(Methylenedioxy)benzaldehyde | | |
| 53 | 3-(4-Methylphenoxy)benzaldehyde | | |
| 54 | 3-(3,4-Dichlorophenoxy)benzaldehyde | | |
| 55 | 3-(3,4-Methoxyphenoxy)benzaldehyde | | |
| 56 | 4-Phenoxybenzaldehyde | | |
| 57 | 3-Phenoxybenzaldehyde | | Boc-p-Iodo-L-Phenylalanine |
| 58 | 4-Biphenylcarboxaldehyde | | |
| 59 | 1-Naphthaldehyde | | |
| 60 | 2-Naphthaldehyde | | |
| 61 | 2-Methoxy-1-Naphthaldehyde | | |
| 62 | 4-Methoxy-1-naphthaldehyde | | Boc-D-Norvaline |
| 63 | | | Boc-D-Norleucine |
| 65 | 9-Ethyl-3-carbazolecarboxaldehyde | | |
| 66 | | | Boc-D-Cyclohexylalanine |
| 67 | 3-Thiophenecarboxaldehyde | | |
| 68 | 5-Methyl-2-thiophenecarboxaldehyde | | Boc-p-Chloro-D-Phenylalanine |
| 69 | 2-Furaldehyde | | |
| 70 | 3-Furaldehyde | | |
| 71 | 5-Methyl-2-furaldehyde | | |
| 72 | | | Boc-β-Thienyl-D-Alanine |
| 73 | | | Boc-O-Ethyl-D-Tyrosine |
| 74 | 3-Pyridinecarboxaldehyde | | Boc-L-Tryptophan |
| 75 | 4-Pyridinecarboxaldehyde | | Boc-D-Trytophan |
| 76 | 6-Methyl-2-pyridinecarbbxaldehyde | | |
| 78 | 1-Methyl-2-pyrrolecarboxaldehyde | | |
| 80 | 1-Methylindole-3-carboxaldehyde | | |
| 84 | 2,6-Dichlorobenzaldehyde | | |
| 85 | 2,3,4-Trimethoxybenzaldehyde | | |
| 87 | 2,3-Dimethyl-p-anisaldehyde | | |
| 88 | 2,4-Dimethoxy-3-methylbenzaldehyde | | |
| 89 | 2,5-Dimethyl-p-anisaldehyde | | |
| 90 | 2-Ethoxybenzaldehyde | | |

TABLE V-continued

| # | ALDEHYDE | ANTHRANILIC ACID DERIVATIVE | AMINO CARBOXYLIC ACID |
|---|---|---|---|
| 92 | 3-(3-(Trifluoromethyl)phenoxy)benzaldehyde | | |
| 93 | 3-(4-t-Butylphenoxy)benzaldehyde | | |
| 94 | 4-(3-Dimethylaminopropoxy)benzaldehyde | | |
| 95 | 5-Bromo-2-Thiophenecarboxaldehyde | | |
| 97 | 4-Benzyloxy-3-methoxybenzaldehyde | | |
| 98 | 4-Stilbenecarboxaldehyde | | |

1. Coupling of Amino Acid to MBHA Resin

The thirty five diverse amino acids provided in Table V, varying at R1, were all coupled to MBHA resin following as follows. 100 mg p-methylbenzhydrylamine (MBHA) resin (0.9 meq/g, 100–200 mesh) was contained within a sealed 1"×1" polypropylene mesh packet (74μ) (tea-bag). Reactions were carried out in a 25 ml polyethylene bottle. Following neutralization with 5% diisopropylamine (DIEA) in dichloromethane (DCM) (3×15 ml), the resin was washed with DCM (2×15 ml). A solution of 0.2M Boc-alanine and 0.2M hydroxybenzotriazole (HOBt) in dimethylformamide (DMF) (4.5 ml, 10×) was added. A solution of 0.2M diisopropylcarbodiimide (DIPCDI) in (4.5 ml, 10×), a condensing agent, was added and allowed to react overnight (16 hr) on a reciprocating shaker. Following washes with DMF (1×15 ml) and DCM (2×15 ml), the Boc protecting group was removed by a 30 minute treatment with 55% trifluoroacetic acid in DCM (15 ml). The resin was then washed with DCM (1×15 ml), isopropanol (IPA) (2×15 ml), and DCM (2×15 ml).

2. Ouinazolinone Library By Condensation of Anthranilic Acids to the Mixture of Resin Bound Amino Acids Fifteen anthranilic acids, each differing by their $R^2$ and listed in Table V, were condensed to the above prepared mixture of resin bound Boc-AAs, followed by acetylation and condensation to form the respective quinazolinone library.

a. Anthranilic Acid Coupling

Following neutralization of the amino acid resin with 5% DIEA in DCM (3×15 ml), the resin was washed with DCM (3×15 ml). A solution of 0.2M anthranilic acid and 0.2M HOBt in DMF (4.5 ml, 10×) was added. A solution of 0.2M DIPCDI (4.5 ml, 10×) was added and allowed to react overnight (16 hr) on a reciprocating shaker. The resin was then washed with DMF (1×15 ml) and DCM (2×15 ml).

b. Acetylation

A solution of 0.5M acetic anhydride (40×) and 1M DIEA (80×) in DMF (7.2 ml) was added. The solution was heated to 80° C. for 3 hr. The resin was then washed with DMF (1×15 ml) and DCM (3×15 ml).

C. Condensation To Close The Ouinazolinone Ring

Condensation was carried out by heating the resin at 80° C. in 2M POCl₃ in 1,4-dioxane (4.5 ml, 100×) for 3 hr. The resin was then washed with 1,4-dioxane (15 ml), followed by three alternating washes with DCM and methanol (15 ml).

3. Stryryl Derivatives of the Ouinazolinones

From the above library of quinazolinones a library of styryl derivatives of quinazolinones were prepared as follows.

In a glove box under a nitrogen atmosphere, the resin was washed with anhydrous tetrahydrofuran (THF) (2×15 ml), 0.2M lithium t-butoxide (LiOtBu) in THF (1×15 ml), and THF (2×15 ml). The resin was allowed to react overnight (16 hr with 0.25M benzaldehyde (25×) and 0.1M LiOtBu (10×) in THF (9 ml). The resin was again washed with anhydrous tetrahydrofuran (THF) (2×15 ml), 0.2M lithium t-butoxide (LiOtBu) in THF (1×15 ml), and THF (2×15 ml). The resin was again allowed to react overnight (16 hr) with 0.25M benzaldehyde (25×) and 0.1M LiOtBu (10×) in THF (9 ml). The resin was then washed with THF (2×15 ml), followed by three alternating washes with DCM and methanol (15 ml).

The resin was then cleaved with 92.5% HF/7.5% anisole (5 ml, 1.5 hr), followed by extraction and lyophilization of product.

Following these procedures a library for a library, containing approximately 35,700 styryl derivatives of quinazolinone were successfully prepared.

Although the invention has been described with reference to the examples provided above, it should be understood that various modifications can be made by those skilled in the art without departing from the invention. Accordingly, the invention is set out in the following claims.

We claim:

1. A combinatorial library of quinazolinones comprising quinazolinones of the structure:

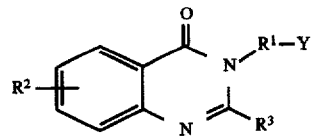

wherein:

$R^1$ is selected from the group consisting of a hydrogen atom, $C_1$ to $C_6$ alkyl; $C_1$ to $C_6$ substituted alkyl, $C_7$ to $C_{12}$ phenylalkyl, $C_7$ to $C_{12}$ substituted phenylalkyl, phenyl, substituted phenyl, $C_3$ to $C_7$ cycloalkyl, and $C_3$ to $C_7$ substituted cycloalkyl;

$R^2$ is selected from the group consisting of a hydrogen atom, halo, hydroxy, protected hydroxy, cyano, nitro, $C_1$ to $C_6$ alkyl, $C_2$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_1$ to $C_4$ alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_3$ to $C_7$ cycloalkenyl, $C_3$ to $C_7$ substituted cycloalkenyl, a heterocyclic ring, $C_7$ to $C_{12}$ phenylalkyl, $C_7$ to $C_{12}$ substituted phenylalkyl, phenyl, substituted phenyl cyclic $C_2$ to $C_{10}$ alkylene, substituted cyclic $C_2$ to $C_{10}$ alkylene, cyclic $C_2$ to $C_{10}$ heteroalkylene, substituted cyclic $C_2$ to $C_{10}$ heteroalkylene, carboxy, protected carboxy, hydroxymethyl, protected hydroxymethyl, (monosubstituted)amino, protected (monosubstituted) amino, (disubstituted)amino, carboxamide, protected carboxamide, $C_1$ to $C_4$ alkylthio, $C_1$ to $C_4$ alkylsulfonyl, methylsulfonylamino, $C_1$ to $C_4$ alkylsulfoxide, phenylthio, substituted phenylthio, phenylsulfoxide, substituted phenylsulfoxide, phenylsulfonyl, and substituted phenylsulfonyl;

$R^3$ is selected from the group consisting of $C_1$ to $C_6$ alkyl, $C_2$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_3$ to $C_7$ cycloalkyl, $C_3$ to $C_7$ substituted cycloalkyl, $C_7$ to $C_{12}$ phenylalkyl, $C_7$ to $C_{12}$ substituted phenylalkyl, phenyl, and substituted phenyl;

Y may be absent and, if present, is selected from the group consisting of a carboxylic acid, carboxamide, protected carboxamide, an amino resin, a hydroxy resin, methylamine, and N-alkylated methylamine.

2. The combinatorial library of claim 1, wherein $R^1$ is selected from the group consisting of the α-carbon and side chain of an amino acid as provided in Table I, n-prop-1,3-yl, n-prop-1,1-yl, n-pent-1,5-yl, n-hex-1,6-yl, p-benzyl, 2-chloro-p-phenyl, p-phenyl, 2-methyl-m-phenyl, 2-hydroxy-p-phenyl, and 2-(phenyl)-n-prop-1,3-yl;

$R^2$ is selected from the group consisting of a hydrogen atom, halo, 6,8-dimethyl, 6-hydroxyl, and a 1,4-butadienyl moiety such that a naphthyl ring results; and $R^3$ is methyl.

3. The combinatorial library of claim 2, wherein $R^2$ is a halo which is selected from the groups consisting of 6,7-difluoro, 6,8-dichloro, and 6,8-dibromo.

4. The combinatorial library of claim 1, wherein $R^1$ is selected from the group consisting of the α-carbon and side chain of an amino acid as provided in Table II;

$R^2$ is selected from the group consisting of a hydrogen atom, 6,8-dimethyl, a 1,4-butadienyl moiety such that a naphthyl ring results, 8-hydoxy, 8-methoxy, 8-methyl, 6-methyl, and halo; and $R^3$ is methyl.

5. The combinatorial library of claim 4, wherein $R^2$ is a halo which is selected from the group consisting of 7,8-difluoro, 5, 6, 7, 8-tetrafluoro, 7-chloro, 7-fluoro, 6-fluoro, 6-chloro, 6-bromo and 6-iodo.

6. A combinatorial library of quinazolinone derivatives comprising quinazolinone derivatives of the structure:

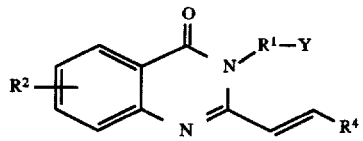

wherein:

$R^1$ is selected from the group consisting of a hydrogen atom, $C_1$ to $C_6$ alkyl; $C_1$ to $C_6$ substituted alkyl, $C_7$ to $C_{12}$ phenylalkyl, $C_7$ to $C_{12}$ substituted phenylalkyl, phenyl, substituted phenyl, $C_3$ to $C_7$ cycloalkyl, and $C_3$ to $C_7$ substituted cycloalkyl;

$R^2$ is selected from the group consisting of a hydrogen atom, halo, hydroxy, protected hydroxy, cyano, nitro, $C_1$ to $C_6$ alkyl, $C_2$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_1$ to $C_4$ alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_3$ to $C_7$ cycloalkenyl, $C_3$ to $C_7$ substituted cycloalkenyl, a heterocyclic ring, $C_7$ to $C_{12}$ phenylalkyl, $C_7$ to $C_{12}$ substituted phenylalkyl, phenyl, substituted phenyl, cyclic $C_2$ to $C_{10}$ alkylene, substituted cyclic $C_2$ to $C_{10}$ alkylene, cyclic $C_2$ to $C_{10}$ heteroalkylene, substituted cyclic $C_2$ to $C_{10}$ heteroalkylene, carboxy, protected carboxy, hydroxymethyl, protected hydroxymethyl, (monosubstituted)amino, protected (monosubstituted) amino, (disubstituted)amino, carboxamide, protected carboxamide, $C_1$ to $C_4$ alkylthio, $C_1$ to $C_4$ alkylsulfonyl, methylsulfonylamino, C1 to C4 alkylsulfoxide, phenylthio, substituted phenylthio, phenylsulfoxide, substituted phenylsulfoxide, phenylsulfonyl, and substituted phenylsulfonyl;

$R^4$ is selected from the group consisting of $C_1$ to $C_6$ alkyl; $C_1$ to $C_6$ substituted alkyl, $C_7$ to $C_{12}$ phenylalkyl, $C_7$ to $C_{12}$ substituted phenylalkyl, phenyl, substituted phenyl, naphthyl, substituted naphthyl, a heterocyclic ring, and a cyclic $C_2$ to $C_{10}$ heteroalkylene;

Y may be absent and, if present, is selected from the group consisting of carboxylic acid, carboxamide, protected carboxamide, an amino resin, a hydroxy resin, methylamine, and N-alkylated methylamine.

7. The combinatorial library of claim 6, wherein $R^1$ is selected from the group consisting of the α-carbon and side chain of an amino acid as provided in Table I, m-prop-1,3-yl, n-prop-1,1-yl, N-pent-1,5-yl, m-hex-1, 6-yl, p-benzyl, 2-chloro-p-phenyl, p-phenyl, 2-methyl-m-phenyl, 2-hydroxy-p-phenyl, and 2-(phenyl)-n-prop-1,3-yl;

$R^2$ is selected from the group consisting of a hydrogen atom, 6,7-difluoro, 6,8-dichloro, 6,8-dibromo, 6,8-dimethyl, 6-hydroxy, and a 1,4-butadienyl moiety such that a naphthyl ring results;

$R^4$ is selected from the groups consisting of phenyl, 2,4-dichlorophenyl, 2-naphthyl, 2,5-dimethylphenyl, 3,4-difluorophenyl, 4-bromophenyl, 3-(4-methylphenoxy)phenyl, 4-methoxyphenyl, biphenyl, 6-methyl-pyridin-2-yl, 2-(methoxy)-naphthyl, 2,4,5,-trimethoxyphenyl, and 4-(dimethylamino)phenyl; and Y may be absent and, if present, is selected from the group consisting of carboxylic acid, carboxamide, protected carboxamide, an amino resin, a hydroxy resin, methylamine, and N-alkylated methylamine.

8. The combinatorial library of claim 6, wherein $R^1$ is selected from the group consisting of the α-carbon and side chain of an amino acid as provided in Table II;

$R^2$ is selected from the group consisting of a hydrogen atom, 6,8-dimethyl, a 1,4-butadienyl moiety such that a naphthyl ring results, 8-hydoxy, 8-methoxy, 8-methyl, 6-methyl, and halo;

$R^4$ is selected from the group consisting of phenyl, 2-bromophenyl, 2-fluorophenyl, 2-methoxyphenyl, 3-bromophenyl, 3-cyanophenyl, 3-fluorophenyl, 3-methoxyphenyl, 3-methylphenyl, 3-(trifluoromethyl) phenyl, 4-bromophenyl, 4-cyanophenyl, 4-fluorophenyl, 4-(dimethylamino)phenyl, 4-isopropylphenyl, 4-methoxyphenyl, 4-methylbenzoate, 4-(methylthio)phenyl, 4-propoxyphenyl, 4-(trifluoromethyl)phenyl, 3,5-dimethoxyphenyl, 2,3-difluorophenyl, 2,5-dimethylphenyl, 2,4-dichlorophenyl, 2-chloro-6-fluorophenyl, 3-bromo-4-fluorophenyl, 3,4- dibenzyloxyphenyl, 3,4-dichlorophenyl, 3,4-difluorophenyl, 3-fluoro-4-methoxyphenyl, 3-methyl-4-methoxyphenyl, 2,3,5-trichlorophenyl, 2,4 5-trimethoxyphenyl, 1, 4-phenyldioxan-6-yl, 3, 4-(methylenedioxy)phenyl, 3-(4-methylphenoxy) phenyl, 3-(3, 4-dichlorophenoxy)phenyl, 3-(3, 4-methoxyphenoxy)phenyl, 4-phenoxyphenyl, 3-phenoxyphenyl, biphenyl, 1-naphthyl, 2-naphthyl, 2-(methoxy)-naphthyl, 4-(methoxy)-naphthyl, 9-ethyl-3-carbozoyl, thiofuranyl, 5-methyl-thiofuran-2-yl, furan-2-yl, furan-3-yi, 5-methyl-furan-2-yl, pyridin-3-yl, pyridin-4-yl, 6-methyl-pyridin-2-yl, 1-methyl-pyrrol-2-yl, 1-methylindo-3-yl, 2,6-dichlorophenyl, 2,3,4-trimethoxyphenyl, 2,3-dimethyl-4-methoxyphenyl, 2,4-dimethoxy-3-methylphenyl, 2,5-dimethyl-4-methoxyphenyl, 2-ethoxyphenyl, 3-(3-trifluoromethyl)phenoxyphenyl, 3-(4-t-butylphenoxy) phenyl, 4-(3-dimethylaminopropoxy)phenyl, 5-bromo-thiofuran-2-yl, 4-benzyloxy-3-methoxyphenyl, and 4-stilbenephenyl; and Y may be absent and, if present, is selected from the group consisting of carboxylic acid, carboxamide, protected carboxamide, an amino resin, a hydroxy resin, methylamine, and N-alkylated methylamine.

9. The combinatorial library of claim 8, wherein $R^2$ is a halo which is selected from the group consisting of 7,8-difluoro, 5, 6, 7, 8-tetrafluoro, 7-chloro, 7-fluoro, 6-fluoro, 6-chloro, 6-bromo and 6-iodo.

10. A combinatorial library of 1,2-dihydro quinazolinone derivatives comprising quinazolinone derivatives of the structure:

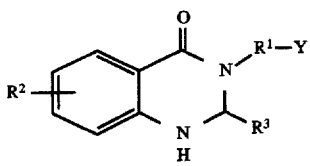

wherein:
- $R^1$ is selected from the group consisting of a hydrogen atom, $C_1$ to $C_6$ alkyl; $C_1$ to $C_6$ substituted alkyl, $C_7$ to $C_{12}$ phenylalkyl, $C_7$ to $C_{12}$ substituted phenylalkyl, phenyl, substituted phenyl, $C_3$ to $C_7$ cycloalkyl, and $C_3$ to $C_7$ substituted cycloalkyl;
- $R^2$ is selected from the group consisting of a hydrogen atom, halo, hydroxy, protected hydroxy, cyano, nitro, $C_1$ to $C_6$ alkyl, $C_2$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_1$ to $C_4$ alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_3$ to $C_7$ cycloalkenyl, $C_3$ to $C_7$ substituted cycloalkenyl, a heterocyclic ring, $C_7$ to $C_{12}$ phenylalkyl, $C_7$ to $C_{12}$ substituted phenylalkyl, phenyl, substituted phenyl, cyclic $C_2$ to $C_{10}$ alkylene, substituted cyclic $C_2$ to $C_{10}$ alkylene, cyclic $C_2$ to $C_{10}$ heteroalkylene, substituted cyclic $C_2$ to $C_{10}$ heteroalkylene, carboxy, protected carboxy, hydroxymethyl, protected hydroxymethyl, (monosubstituted)amino, protected (monosubstituted) amino, (disubstituted) amino, carboxamide, protected carboxamide, $C_1$ to $C_4$ alkylthio, $C_1$ to $C_4$ alkylsulfonyl, methylsulfonylamino, $C_1$ to $C_4$ alkylsulfoxide, phenylthio, substituted phenylthio, phenylsulfoxide, substituted phenylsulfoxide, phenylsulfonyl, and substituted phenylsulfonyl;
- $R^3$ is selected from the group consisting of $C_1$ to $C_6$ alkyl, $C_2$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_3$ to $C_7$ cycloalkyl, $C_3$ to $C_7$ substituted cycloalkyl, $C_7$ to $C_{12}$ phenylalkyl, $C_7$ to $C_{12}$ substituted phenylalkyl, phenyl, and substituted phenyl;

Y may be absent and, if present, is selected from the group consisting of a carboxylic acid, carboxamide, protected carboxamide, an amino resin, a hydroxy resin, methylamine, and N-alkylated methylamine.

11. A combinatorial library of quinazolinone derivatives comprising quinazolinone derivatives of the structure:

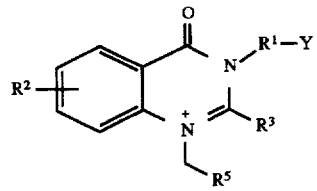

wherein:
- $R^1$ is selected from the group consisting of a hydrogen atom, $C_1$ to $C_6$ alkyl; $C_1$ to $C_6$ substituted alkyl, $C_7$ to $C_{12}$ phenylalkyl, $C_7$ to $C_{12}$ substituted phenylalkyl, phenyl, substituted phenyl, $C_3$ to $C_7$ cycloalkyl, and $C_3$ to $C_7$ substituted cycloalkyl;
- $R^2$ is selected from the group consisting of a hydrogen atom, halo, hydroxy, protected hydroxy, cyano, nitro, $C_1$ to $C_6$ alkyl, $C_2$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_1$ to $C_4$ alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_3$ to $C_7$ cycloalkenyl, $C_3$ to $C_7$ substituted cycloalkenyl, a heterocyclic ring, $C_7$ to $C_{12}$ phenylalkyl, $C_7$ to $C_{12}$ substituted phenylalkyl, phenyl, substituted phenyl, cyclic $C_2$ to $C_{10}$ alkylene, substituted cyclic $C_2$ to $C_{10}$ alkylene, cyclic $C_2$ to $C_{10}$ heteroalkylene, substituted cyclic $C_2$ to $C_{10}$ heteroalkylene, carboxy, protected carboxy, hydroxymethyl, protected hydroxymethyl, (monosubstituted)amino, protected (monosubstituted) amino, (disubstituted) amino, carboxamide, protected carboxamide, $C_1$ to $C_4$ alkylthio, $C_1$ to $C_4$ alkylsulfonyl, methylsulfonylamino, C1 to C4 alkylsulfoxide, phenylthio, substituted phenylthio, phenylsulfoxide, substituted phenylsulfoxide, phenylsulfonyl, and substituted phenylsulfonyl
- $R^3$ is selected from the group consisting of $C_1$ to $C_6$ alkyl, $C_1$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_3$ to $C_7$ cycloalkyl, $C_3$ to $C_7$ substituted cycloalkyl, $C_7$ to $C_{12}$ phenylalkyl, $C_7$ to $C_{12}$ substituted phenylalkyl, phenyl, and substituted phenyl;
- $R^5$ is selected from the group consisting of $C_1$ to $C_6$ alkyl; $C_1$ to $C_6$ substituted alkyl, $C_1$ to $C_4$ alkoxy, $C_7$ to $C_{12}$ phenylalkyl, $C_7$ to $C_{12}$ substituted phenylalkyl, phenyl, and substituted phenyl;

Y may be absent and, if present, is selected from the group consisting of a carboxylic acid, carboxamide, protected carboxamide, an amino resin, a hydroxy resin, methylamine, and N-alkylated methylamine.

12. A combinatorial library of quinazolinone derivatives comprising quinazolinone derivatives of the structure:

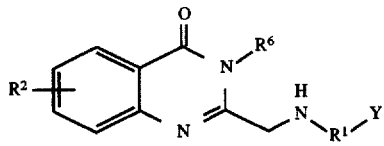

wherein:

R¹ is selected from the group consisting of a hydrogen atom, $C_1$ to $C_6$ alkyl; $C_1$ to $C_6$ substituted alkyl, $C_7$ to $C_{12}$ phenylalkyl, $C_7$ to $C_{12}$ substituted phenylalkyl, phenyl, substituted phenyl, $C_3$ to $C_7$ cycloalkyl, and $C_3$ to $C_7$ substituted cycloalkyl;

R² is selected from the group consisting of a hydrogen atom, halo, hydroxy, protected hydroxy, cyano, nitro, $C_1$ to $C_6$ alkyl, $C_2$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_1$ to $C_4$ alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_3$ to $C_7$ cycloalkenyl, $C_3$ to $C_7$ substituted cycloalkenyl, a heterocyclic ring, $C_7$ to $C_{12}$ phenylalkyl, $C_7$ to $C_{12}$ substituted phenylalkyl, phenyl, substituted phenyl, cyclic $C_2$ to $C_{10}$ alkylene, substituted cyclic $C_2$ to $C_{10}$ alkylene, cyclic $C_2$ to $C_{10}$ heteroalkylene, substituted cyclic $C_2$ to $C_{10}$ heteroalkylene, carboxy, protected carboxy, hydroxymethyl, protected hydroxymethyl, (monosubstituted)amino, protected (monosubstituted) amino, (disubstituted) amino, carboxamide, protected carboxamide, $C_1$ to $C_4$ alkylthio, $C_1$ to $C_4$ alkylsulfonyl, methylsulfonylamino, C1 to C4 alkylsulfoxide, phenylthio, substituted phenylthio, phenylsulfoxide, substituted phenylsulfoxide, phenylsulfonyl, and substituted phenylsulfonyl;

R⁶ is selected from the group consisting of a hydrogen atom, $C_1$ to $C_6$ alkyl; $C_1$ to $C_6$ substituted alkyl, $C_7$ to $C_{12}$ phenylalkyl, $C_7$ to $C_{12}$ substituted phenylalkyl, phenyl, substituted phenyl, $C_3$ to $C_7$ cycloalkyl, $C_3$ to $C_7$ substituted cycloalkyl, carboxylic acid, carboxamide, and protected carboxamide;

Y may be absent and, if present, is selected from the group consisting of a carboxylic acid, carboxamide, protected carboxamide, an amino resin, a hydroxy resin, methylamine, and N-alkylated methylamine.

13. A combinatorial library of quinazolinone derivatives comprising quinazolinone derivatives of the structure:

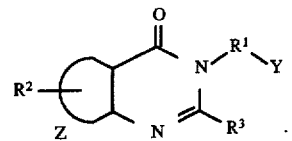

wherein:

R¹ is selected from the group consisting of a hydrogen atom, $C_1$ to $C_6$ alkyl; $C_1$ to $C_6$ substituted alkyl, $C_7$ to $C_{12}$ phenylalkyl, $C_7$ to $C_{12}$ substituted phenylalkyl, phenyl, substituted phenyl, $C_3$ to $C_7$ cycloalkyl, and $C_3$ to $C_7$ substituted cycloalkyl;

R² is selected from the group consisting of a hydrogen atom, halo, hydroxy, protected hydroxy, cyano, nitro, $C_1$ to $C_6$ alkyl, $C_2$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_1$ to $C_4$ alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_3$ to $C_7$ cycloalkenyl, $C_3$ to $C_7$ substituted cycloalkenyl, a heterocyclic ring, $C_7$ to $C_{12}$ phenylalkyl, $C_7$ to $C_{12}$ substituted phenylalkyl, phenyl, substituted phenyl, cyclic $C_2$ to $C_{10}$ alkylene, substituted cyclic $C_2$ to $C_{10}$ alkylene, cyclic $C_2$ to $C_{10}$ heteroalkylene, substituted cyclic $C_2$ to $C_{10}$ heteroalkylene, carboxy, protected carboxy, hydroxymethyl, protected hydroxymethyl, (monosubstituted)amino, protected (monosubstituted) amino, (disubstituted)amino, carboxamide, protected carboxamide, $C_1$ to $C_4$ alkylthio, $C_1$ to $C_4$ alkylsulfonyl, methylsulfonylamino, C1 to C4 alkylsulfoxide, phenylthio, substituted phenylthio, phenylsulfoxide, substituted phenylsulfoxide, phenylsulfonyl, and substituted phenylsulfonyl;

R³ is selected from the group consisting of $C_1$ to $C_6$ alkyl, $C_2$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_3$ to $C_7$ cycloalkyl, $C_3$ to $C_7$ substituted cycloalkyl, $C_7$ to $C_{12}$ phenylalkyl, $C_7$ to $C_{12}$ substituted phenylalkyl, phenyl, and substituted phenyl;

Y may be absent and, if present, is selected from the group consisting of a carboxylic acid, carboxamide, protected carboxamide, an amino resin, a hydroxy resin, methylamine, and N-alkylated methylamine;

Z is a heteroaromatic ring having from two to six carbons and one or two heteroatoms selected from the group consisting of nitrogen, sulfur and oxygen.

14. The combinatorial library of claim 13, wherein Z is selected from the group consisting of pyridino ring and pyrazino ring.

* * * * *